United States Patent
Glorioso et al.

(10) Patent No.: US 6,228,356 B1
(45) Date of Patent: *May 8, 2001

(54) VIRAL VECTORS TO INHIBIT LEUKOCYTE INFILTRATION OR CARTILAGE DEGRADATION OF JOINTS

(75) Inventors: Joseph C. Glorioso, Cheswick; Christopher H. Evans; Paul D. Robbins, both of Pittsburgh, all of PA (US); Geethani Bandara, Milburn, NJ (US)

(73) Assignee: University of Pittsburgh of the Commonwealth System of Higher Education

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/685,212

(22) Filed: Jul. 23, 1996

Related U.S. Application Data

(63) Continuation of application No. 08/027,750, filed on Mar. 8, 1993, now abandoned, which is a continuation-in-part of application No. 07/963,928, filed on Oct. 20, 1992, now abandoned, which is a continuation of application No. 07/630,981, filed on Dec. 20, 1990, now abandoned.

(51) Int. Cl.[7] .............................. A01N 63/00; A61K 48/00
(52) U.S. Cl. ........................................... 424/93.2; 424/93.6
(58) Field of Search .............................. 514/44; 424/93.1, 424/93.21, 93.2, 93.6; 435/320.1, 325, 455

(56) References Cited

U.S. PATENT DOCUMENTS

| | | | |
|---|---|---|---|
| 4,396,601 | 8/1983 | Salser et al. | 424/94 |
| 4,766,069 | 8/1988 | Auron et al. | 435/70 |
| 4,778,806 | 10/1988 | Bender et al. | 514/336 |
| 4,780,470 | 10/1988 | Bender et al. | 514/341 |
| 4,794,114 | 12/1988 | Bender et al. | 514/333 |
| 4,816,436 | 3/1989 | Jacobs | 514/2 |
| 4,870,101 | 9/1989 | Ku et al. | 514/476 |
| 4,935,343 | 6/1990 | Allison et al. | 435/7 |
| 4,968,607 | 11/1990 | Dower et al. | 435/69.1 |
| 5,081,228 | * 1/1992 | Dower . | |
| 5,180,812 | * 1/1993 | Dower et al. . | |

FOREIGN PATENT DOCUMENTS 9211359   7/1992  (WO) .

OTHER PUBLICATIONS

Chin and Horuk, 1990, Interleukin 1 Receptors on Rabbit Articular Chondrocytes: Relationship Between Biological Activity and Receptor Binding Kinetics. The FASEB J. 4:1481–1487.

Banerjee, et al., 1988, Immunosupression of Collagen–Induced Arthritis in Mice With an Anti–IL–2 Receptor Antibody, J. Immunology 141:1150–1154.

Fanslow, et al., 1990, Regulation of Alloreactivity In Vivo by a Soluble Form of the Interleukin–1 Receptor, Science 248: 739–742.

Pettipher, et al., 1986, Interleukin–1 induces Leukocyte Infiltration and Cartilage Proteoglycan Degradation In Synovial Joint, Proc. Natl. Acad. Sci. USA 83:8749–8753.

Rosenberg, et al. 1988, Grafting Genetically Modified Cells to the Damaged Brain: Retroactive Effects of NGF Expression, Science 242: 1575–1578.

Bandara, et al, 1992, Gene Transfer to Synoviocytes: Prospects for Gene Treatment of Arthritis, DNA and Cell Biology 11 (3): 227–231.

Evans, et al., 1992, Gene Transfer to Joints for Arthritis Therapy, J. Cell Biochem. 16F:V207.

Evans, 1992, Transferring Therapeutic Genes to Joints: A Pittsburgh Idea, The Pittsburgh Orthopaedic J. 3: 130–131.

Evans, et al., 1992, Synovial Cell Transplants for Gene Transfer to Joints, Transplantation Proceedings 24(6):2966.

Bandara, et al., 1993, Gene Transfer to Synovium, Trans. Orthop. Res. Soc. 18:242.

Bandara, et al., 1992, Intraarticular Expression of IRAP by Gene Transfer, Arthritis Rheum. 39(Supp): s193 (C161).

Gao and Huang, 1991, A Novel Cationic Liposome Reagent for Efficient Transfection of Mammalian Cells, Biochem. and Biophys. Res. Comm. 179:280–285.

Korman, et al, 1987, Expression of Human Class II Major Histocompatibility Complex Antigens Using Retrovirus Vectors, Proc. Natl. Acad. Sci. USA 84:2150–2154.

(List continued on next page.)

*Primary Examiner*—Deborah Crouch
(74) *Attorney, Agent, or Firm*—Townsend & Townsend & Crew LLP

(57) ABSTRACT

The subject invention concerns a method of introducing at least one gene encoding a product into at least one cell of a connective tissue of a mammalian host for use in treating the mammalian host including employing recombinant techniques to produce a DNA vector molecule which contains the gene encoding for the product and infecting the connective cell of the mammalian host using the DNA vector molecule using the gene coding for the product. A method is provided for introducing at least one gene encoding a product into at least one cell of a connective tissue of a mammalian host employing non-viral methods. A method to produce an animal model for the study of connective tissue pathology is also disclosed. Additionally, this invention provides a method of using in vivo a gene encoding and extracellular interleukin-1 binding domain of an interleukin-1 receptor.

9 Claims, 10 Drawing Sheets

OTHER PUBLICATIONS

Danos and Mulligan, 1988, Safe and Efficient Generation of Recombinant Retroviruses With Amphotropic and Ecotropic Host Ranges, Proc. Natl. Acad. Sci. USA 85:6460–6464.
Blau et al (Nov. 2, 1995) New Eng. J. Med., 1204–1207.*
Science, vol. 269, 1995, pp. 1050–1055.*
Bamdara et al. (1993) Proced. Natl. Acad. Sci. 90, 10764–10768.*
Hung et al. (1994) Gene Therapy 1, 64–69.*
Price et al (1987) Proced. Natl. Acad. Sci. 84, 156–160.*
Nicolau et al (1983) Proced. Natl. Acad. Sci. 80, 1068–1072.*
Bandara et al (1993) Proced. Natl. Acad. Sci. 90, 10764–10768.*
Hannum et al (1990) Nature 343, 336–340.*

* cited by examiner

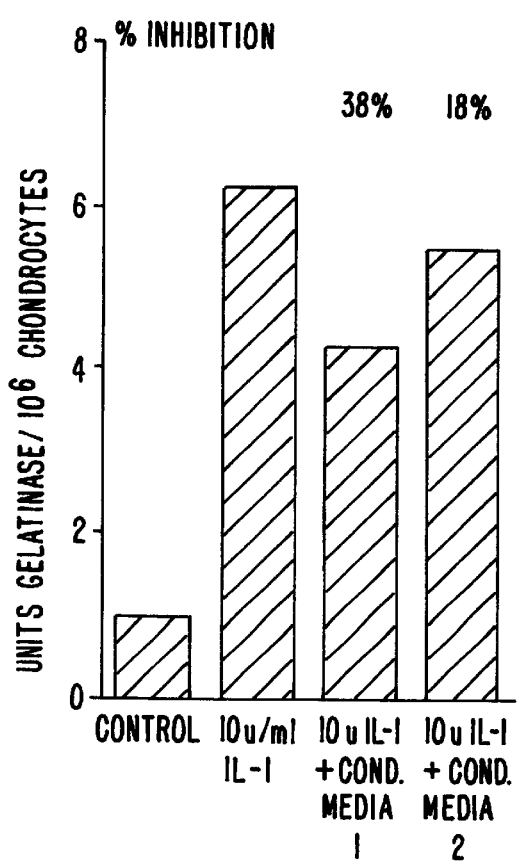
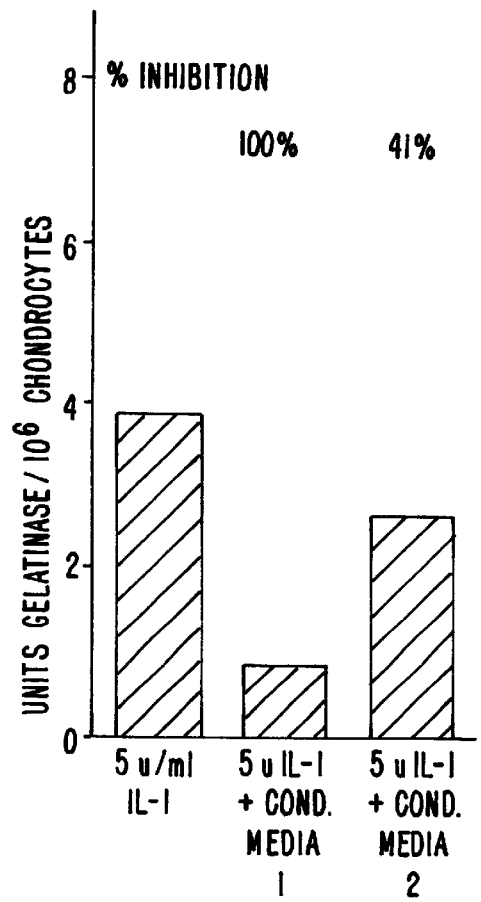
FIG. 5A.                    FIG. 5B.

LTR - Long Terminal Repeats - Regulates Viral Transcription And Expression Of IL - 1 Receptor neo<sup>r</sup> - Bacterial Gene Encoding Resistance To The Antibiotic Neomycin SV 40 - Simian Virus 40 Enhancer Promoter - Regulates Expression Of The neo<sup>r</sup> Gene

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1770 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vii) IMMEDIATE SOURCE:
      (A) LIBRARY: Human T-cell cDNA Library
      (B) CLONE: Human Interleukin-1 Receptor (ix) FEATURE:
      (A) NAME/KEY: CDS
      (B) LOCATION: 55..1764

(xi) SEQUENCE DESCRIPTION: SEQ ID NO:1:

```
CCTCCTGAGA AGCTGGACCC CTTGGTAAAA GACAAGGCCT TCTCCAAGAA GAAT ATG        57
                                                            Met
                                                              1

AAA GTG TTA CTC AGA CTT ATT TGT TTC ATA GCT CTA CTG ATT TCT TCT       105
Lys Val Leu Leu Arg Leu Ile Cys Phe Ile Ala Leu Leu Ile Ser Ser
              5                  10                  15

CTG GAG GCT GAT AAA TGC AAG GAA CGT GAA GAA AAA ATA ATT TTA GTG       153
Leu Glu Ala Asp Lys Cys Lys Glu Arg Glu Glu Lys Ile Ile Leu Val
         20                  25                  30

TCA TCT GCA AAT GAA ATT GAT GTT CGT CCC TGT CCT CTT AAC CCA AAT       201
Ser Ser Ala Asn Glu Ile Asp Val Arg Pro Cys Pro Leu Asn Pro Asn
     35                  40                  45

GAA CAC AAA GGC ACT ATA ACT TGG TAT AAA GAT GAC AGC AAG ACA CCT       249
Glu His Lys Gly Thr Ile Thr Trp Tyr Lys Asp Asp Ser Lys Thr Pro
 50                  55                  60                  65

GTA TCT ACA GAA CAA GCC TCC AGG ATT CAT CAA CAC AAA GAG AAA CTT       297
Val Ser Thr Glu Gln Ala Ser Arg Ile His Gln His Lys Glu Lys Leu
                 70                  75                  80

TGG TTT GTT CCT GCT AAG GTG GAG GAT TCA GGA CAT TAC TAT TGC GTG       345
Trp Phe Val Pro Ala Lys Val Glu Asp Ser Gly His Tyr Tyr Cys Val
             85                  90                  95

GTA AGA AAT TCA TCT TAC TGC CTC AGA ATT AAA ATA AGT GCA AAA TTT       393
Val Arg Asn Ser Ser Tyr Cys Leu Arg Ile Lys Ile Ser Ala Lys Phe
        100                 105                 110

GTG GAG AAT GAG CCT AAC TTA TGT TAT AAT GCA CAA GCC ATA TTT AAG       441
```

-continued

```
Val Glu Asn Glu Pro Asn Leu Cys Tyr Asn Ala Gln Ala Ile Phe Lys
    115                 120                 125

CAG AAA CTA CCC GTT GCA GGA GAC GGA GGA CTT GTG TGC CCT TAT ATG       489
Gln Lys Leu Pro Val Ala Gly Asp Gly Gly Leu Val Cys Pro Tyr Met
130                 135                 140                 145

GAG TTT TTT AAA AAT GAA AAT AAT GAG TTA CCT AAA TTA CAG TGG TAT       537
Glu Phe Phe Lys Asn Glu Asn Asn Glu Leu Pro Lys Leu Gln Trp Tyr
                150                 155                 160

AAG GAT TGC AAA CCT CTA CTT CTT GAC AAT ATA CAC TTT AGT GGA GTC       585
Lys Asp Cys Lys Pro Leu Leu Leu Asp Asn Ile His Phe Ser Gly Val
                165                 170                 175

AAA GAT AGG CTC ATC GTG ATG AAT GTG GCT GAA AAG CAT AGA GGG AAC       633
Lys Asp Arg Leu Ile Val Met Asn Val Ala Glu Lys His Arg Gly Asn
    180                 185                 190

TAT ACT TGT CAT GCA TCC TAC ACA TAC TTG GGC AAG CAA TAT CCT ATT       681
Tyr Thr Cys His Ala Ser Tyr Thr Tyr Leu Gly Lys Gln Tyr Pro Ile
195                 200                 205

ACC CGG GTA ATA GAA TTT ATT ACT CTA GAG GAA AAC AAA CCC ACA AGG       729
Thr Arg Val Ile Glu Phe Ile Thr Leu Glu Glu Asn Lys Pro Thr Arg
210                 215                 220                 225

CCT GTG ATT GTG AGC CCA GCT AAT GAG ACA ATG GAA GTA GAC TTG GGA       777
Pro Val Ile Val Ser Pro Ala Asn Glu Thr Met Glu Val Asp Leu Gly
                230                 235                 240

TCC CAG ATA CAA TTG ATC TGT AAT GTC ACC GGC CAG TTG AGT GAC ATT       825
Ser Gln Ile Gln Leu Ile Cys Asn Val Thr Gly Gln Leu Ser Asp Ile
                245                 250                 255

GCT TAC TGG AAG TGG AAT GGG TCA GTA ATT GAT GAA GAT GAC CCA GTG       873
Ala Tyr Trp Lys Trp Asn Gly Ser Val Ile Asp Glu Asp Asp Pro Val
                260                 265                 270

CTA GGG GAA GAC TAT TAC AGT GTG GAA AAT CCT GCA AAC AAA AGA AGG       921
Leu Gly Glu Asp Tyr Tyr Ser Val Glu Asn Pro Ala Asn Lys Arg Arg
275                 280                 285

AGT ACC CTC ATC ACA GTG CTT AAT ATA TCG GAA ATT GAA AGT AGA TTT       969
Ser Thr Leu Ile Thr Val Leu Asn Ile Ser Glu Ile Glu Ser Arg Phe
290                 295                 300                 305

TAT AAA CAT CCA TTT ACC TGT TTT GCC AAG AAT ACA CAT GGT ATA GAT       1017
Tyr Lys His Pro Phe Thr Cys Phe Ala Lys Asn Thr His Gly Ile Asp
                310                 315                 320

GCA GCA TAT ATC CAG TTA ATA TAT CCA GTC ACT AAT TTC CAG AAG CAC       1065
Ala Ala Tyr Ile Gln Leu Ile Tyr Pro Val Thr Asn Phe Gln Lys His
                325                 330                 335

ATG ATT GGT ATA TGT GTC ACG TTG ACA GTC ATA ATT GTG TGT TCT GTT       1113
Met Ile Gly Ile Cys Val Thr Leu Thr Val Ile Ile Val Cys Ser Val
                340                 345                 350

TTC ATC TAT AAA ATC TTC AAG ATT GAC ATT GTG CTT TGG TAC AGG GAT       1161
Phe Ile Tyr Lys Ile Phe Lys Ile Asp Ile Val Leu Trp Tyr Arg Asp
355                 360                 365

TCC TGC TAT GAT TTT CTC CCA ATA AAA GCT TCA GAT GGA AAG ACC TAT       1209
Ser Cys Tyr Asp Phe Leu Pro Ile Lys Ala Ser Asp Gly Lys Thr Tyr
370                 375                 380                 385

GAC GCA TAT ATA CTG TAT CCA AAG ACT GTT GGG GAA GGG TCT ACC TCT       1257
Asp Ala Tyr Ile Leu Tyr Pro Lys Thr Val Gly Glu Gly Ser Thr Ser
                390                 395                 400

GAC TGT GAT ATT TTT GTG TTT AAA GTC TTG CCT GAG GTC TTG GAA AAA       1305
Asp Cys Asp Ile Phe Val Phe Lys Val Leu Pro Glu Val Leu Glu Lys
                405                 410                 415

CAG TGT GGA TAT AAG CTG TTC ATT TAT GGA AGG GAT GAC TAC GTT GGG       1353
Gln Cys Gly Tyr Lys Leu Phe Ile Tyr Gly Arg Asp Asp Tyr Val Gly
                420                 425                 430
```

```
GAA GAC ATT GTT GAG GTC ATT AAT GAA AAC GTA AAG AAA AGC AGA AGA      1401
Glu Asp Ile Val Glu Val Ile Asn Glu Asn Val Lys Lys Ser Arg Arg
        435                 440                 445

CTG ATT ATC ATT TTA GTC AGA GAA ACA TCA GGC TTC AGC TGG CTG GGT      1449
Leu Ile Ile Ile Leu Val Arg Glu Thr Ser Gly Phe Ser Trp Leu Gly
450                 455                 460                 465

GGT TCA TCT GAA GAG CAA ATA GCC ATG TAT AAT GCT CTT GTT CAG GAT      1497
Gly Ser Ser Glu Glu Gln Ile Ala Met Tyr Asn Ala Leu Val Gln Asp
                470                 475                 480

GGA ATT AAA GTT GTC CTG CTT GAG CTG GAG AAA ATC CAA GAC TAT GAG      1545
Gly Ile Lys Val Val Leu Leu Glu Leu Glu Lys Ile Gln Asp Tyr Glu
            485                 490                 495

AAA ATG CCA GAA TCG ATT AAA TTC ATT AAG CAG AAA CAT GGG GCT ATC      1593
Lys Met Pro Glu Ser Ile Lys Phe Ile Lys Gln Lys His Gly Ala Ile
500                 505                 510

CGC TGG TCA GGG GAC TTT ACA CAG GGA CCA CAG TCT GCA AAG ACA AGG      1641
Arg Trp Ser Gly Asp Phe Thr Gln Gly Pro Gln Ser Ala Lys Thr Arg
    515                 520                 525

TTC TGG AAG AAT GTC AGG TAC CAC ATG CCA GTC CAG CGA CGG TCA CCT      1689
Phe Trp Lys Asn Val Arg Tyr His Met Pro Val Gln Arg Arg Ser Pro
530                 535                 540                 545

TCA TCT AAA CAC CAG TTA CTG TCA CCA GCC ACT AAG GAG AAA CTG CAA      1737
Ser Ser Lys His Gln Leu Leu Ser Pro Ala Thr Lys Glu Lys Leu Gln
                550                 555                 560

AGA GAG GCT CAC GTG CCT CTC GGG TAGCATGGA                            1770
Arg Glu Ala His Val Pro Leu Gly
            565                 570

(2) INFORMATION FOR SEQ ID NO:2:

(i) SEQUENCE CHARACTERISTICS:
        (A) LENGTH: 569 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
```

```
                    165                 170                 175
Val Lys Asp Arg Leu Ile Val Met Asn Val Ala Glu Lys His Arg Gly
                180                 185                 190

Asn Tyr Thr Cys His Ala Ser Tyr Thr Tyr Leu Gly Lys Gln Tyr Pro
            195                 200                 205

Ile Thr Arg Val Ile Glu Phe Ile Thr Leu Glu Glu Asn Lys Pro Thr
        210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
            325                 330                 335

His Met Ile Gly Ile Cys Val Thr Leu Thr Val Ile Val Cys Ser
        340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
        370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445

Arg Leu Ile Ile Ile Leu Val Arg Glu Thr Ser Gly Phe Ser Trp Leu
450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
        530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565
```

(2) INFORMATION FOR SEQ ID NO:3:

(i) SEQUENCE CHARACTERISTICS:
    (A) LENGTH: 1782 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (vii) IMMEDIATE SOURCE:
    (A) LIBRARY: Mouse T-cell cDNA Library
    (B) CLONE: Mouse Interleukin-1 Receptor (ix) FEATURE:
    (A) NAME/KEY: CDS
    (B) LOCATION: 46..1776

(xi) SEQUENCE DESCRIPTION: SEQ ID NO:3:

```
GGATGTCATC AGAGTTCCCA GTGCCCCGAA CCGTGAACAA CACAA ATG GAG AAT            54
                                                 Met Glu Asn
                                                   1

ATG AAA GTG CTA CTG GGG CTC ATT TGT CTC ATG GTG CCT CTG CTG TCG         102
Met Lys Val Leu Leu Gly Leu Ile Cys Leu Met Val Pro Leu Leu Ser
      5                  10                  15

CTG GAG ATT GAC GTA TGT ACA GAA TAT CCA AAT CAG ATC GTT TTG TTT         150
Leu Glu Ile Asp Val Cys Thr Glu Tyr Pro Asn Gln Ile Val Leu Phe
 20                  25                  30                  35

TTA TCT GTA AAT GAA ATT GAT ATT CGC AAG TGT CCT CTT ACT CCA AAT         198
Leu Ser Val Asn Glu Ile Asp Ile Arg Lys Cys Pro Leu Thr Pro Asn
                 40                  45                  50

AAA ATG CAC GGC GAC ACC ATA ATT TGG TAC AAG AAT GAC AGC AAG ACC         246
Lys Met His Gly Asp Thr Ile Ile Trp Tyr Lys Asn Asp Ser Lys Thr
             55                  60                  65

CCC ATA TCA GCG GAC CGG GAC TCC AGG ATT CAT CAG CAG AAT GAA CAT         294
Pro Ile Ser Ala Asp Arg Asp Ser Arg Ile His Gln Gln Asn Glu His
         70                  75                  80

CTT TGG TTT GTA CCT GCC AAG GTG GAG GAC TCA GGA TAT TAC TAT TGT         342
Leu Trp Phe Val Pro Ala Lys Val Glu Asp Ser Gly Tyr Tyr Tyr Cys
     85                  90                  95

ATA GTA AGA AAC TCA ACT TAC TGC CTC AAA ACT AAA GTA ACC GTA ACT         390
Ile Val Arg Asn Ser Thr Tyr Cys Leu Lys Thr Lys Val Thr Val Thr
100                 105                 110                 115

GTG TTA GAG AAT GAC CCT GGC TTG TGT TAC AGC ACA CAG GCC ACC TTC         438
Val Leu Glu Asn Asp Pro Gly Leu Cys Tyr Ser Thr Gln Ala Thr Phe
120                 125                 130

CCA CAG CGG CTC CAC ATT GCC GGG GAT GGA AGT CTT GTG TGC CCT TAT         486
Pro Gln Arg Leu His Ile Ala Gly Asp Gly Ser Leu Val Cys Pro Tyr
                135                 140                 145

GTG AGT TAT TTT AAA GAT GAA AAT AAT GAG TTA CCC GAG GTC CAG TGG         534
Val Ser Tyr Phe Lys Asp Glu Asn Asn Glu Leu Pro Glu Val Gln Trp
            150                 155                 160

TAT AAG AAC TGT AAA CCT CTG CTT CTT GAC AAC GTG AGC TTC TTC GGA         582
Tyr Lys Asn Cys Lys Pro Leu Leu Leu Asp Asn Val Ser Phe Phe Gly
        165                 170                 175

GTA AAA GAT AAA CTG TTG GTG AGG AAT GTG GCT GAA GAG CAC AGA GGG         630
Val Lys Asp Lys Leu Leu Val Arg Asn Val Ala Glu Glu His Arg Gly
180                 185                 190                 195

GAC TAT ATA TGC CGT ATG TCC TAT ACG TTC CGG GGG AAG CAA TAT CCG         678
Asp Tyr Ile Cys Arg Met Ser Tyr Thr Phe Arg Gly Lys Gln Tyr Pro
                200                 205                 210
```

```
                                                                -continued

GTC ACA CGA GTA ATA CAA TTT ATC ACA ATA GAT GAA AAC AAG AGG GAC      726
Val Thr Arg Val Ile Gln Phe Ile Thr Ile Asp Glu Asn Lys Arg Asp
        215                 220                 225

AGA CCT GTT ATC CTG AGC CCT CGG AAT GAG ACG ATC GAA GCT GAC CCA      774
Arg Pro Val Ile Leu Ser Pro Arg Asn Glu Thr Ile Glu Ala Asp Pro
            230                 235                 240

GGA TCA ATG ATA CAA CTG ATC TGC AAC GTC ACG GGC CAG TTC TCA GAC      822
Gly Ser Met Ile Gln Leu Ile Cys Asn Val Thr Gly Gln Phe Ser Asp
    245                 250                 255

CTT GTC TAC TGG AAG TGG AAT GGA TCA GAA ATT GAA TGG AAT GAT CCA      870
Leu Val Tyr Trp Lys Trp Asn Gly Ser Glu Ile Glu Trp Asn Asp Pro
260                 265                 270                 275

TTT CTA GCT GAA GAC TAT CAA TTT GTG GAA CAT CCT TCA ACC AAA AGA      918
Phe Leu Ala Glu Asp Tyr Gln Phe Val Glu His Pro Ser Thr Lys Arg
                280                 285                 290

AAA TAC ACA CTC ATT ACA ACA CTT AAC ATT TCA GAA GTT AAA AGC CAG      966
Lys Tyr Thr Leu Ile Thr Thr Leu Asn Ile Ser Glu Val Lys Ser Gln
            295                 300                 305

TTT TAT CGC TAT CCG TTT ATC TGT GTT GTT AAG AAC ACA AAT ATT TTT     1014
Phe Tyr Arg Tyr Pro Phe Ile Cys Val Val Lys Asn Thr Asn Ile Phe
    310                 315                 320

GAG TCG GCG CAT GTG CAG TTA ATA TAC CCA GTC CCT GAC TTC AAG AAT     1062
Glu Ser Ala His Val Gln Leu Ile Tyr Pro Val Pro Asp Phe Lys Asn
325                 330                 335

TAC CTC ATC GGG GGC TTT ATC ATC CTC ACG GCT ACA ATT GTA TGC TGT     1110
Tyr Leu Ile Gly Gly Phe Ile Ile Leu Thr Ala Thr Ile Val Cys Cys
340                 345                 350                 355

GTG TGC ATC TAT AAA GTC TTC AAG GTT GAC ATA GTG CTT TGG TAC AGG     1158
Val Cys Ile Tyr Lys Val Phe Lys Val Asp Ile Val Leu Trp Tyr Arg
                360                 365                 370

GAC TCC TGC TCT GGT TTT CTT CCT TCA AAA GCT TCA GAT GGA AAG ACA     1206
Asp Ser Cys Ser Gly Phe Leu Pro Ser Lys Ala Ser Asp Gly Lys Thr
            375                 380                 385

TAC GAT GCA TAT ATT CTT TAT CCC AAG ACC CTG GGA GAG GGG TCC TTC     1254
Tyr Asp Ala Tyr Ile Leu Tyr Pro Lys Thr Leu Gly Glu Gly Ser Phe
        390                 395                 400

TCA GAC TTA GAT ACT TTT GTT TTT AAA CTG TTG CCT GAG GTC TTG GAG     1302
Ser Asp Leu Asp Thr Phe Val Phe Lys Leu Leu Pro Glu Val Leu Glu
405                 410                 415

GGA CAG TTT GGA TAC AAG CTG TTC ATT TAT GGA AGG GAT GAC TAT GTT     1350
Gly Gln Phe Gly Tyr Lys Leu Phe Ile Tyr Gly Arg Asp Asp Tyr Val
420                 425                 430                 435

GGA GAA GAT ACC ATC GAG GTT ACT AAT GAA AAT GTA AAG AAA AGC AGG     1398
Gly Glu Asp Thr Ile Glu Val Thr Asn Glu Asn Val Lys Lys Ser Arg
                440                 445                 450

AGG CTG ATT ATC ATT CTA GTG AGA GAT ATG GGA GGC TTC AGC TGG CTG     1446
Arg Leu Ile Ile Ile Leu Val Arg Asp Met Gly Gly Phe Ser Trp Leu
            455                 460                 465

GGC CAG TCA TCT GAA GAG CAA ATA GCC ATA TAC AAT GCT CTC ATC CAG     1494
Gly Gln Ser Ser Glu Glu Gln Ile Ala Ile Tyr Asn Ala Leu Ile Gln
        470                 475                 480

GAA GGA ATT AAA ATC GTC CTG CTT GAG TTG GAG AAA ATC CAA GAC TAT     1542
Glu Gly Ile Lys Ile Val Leu Leu Glu Leu Glu Lys Ile Gln Asp Tyr
485                 490                 495

GAG AAA ATG CCA GAT TCT ATT CAG TTC ATT AAG CAG AAA CAC GGA GTC     1590
Glu Lys Met Pro Asp Ser Ile Gln Phe Ile Lys Gln Lys His Gly Val
500                 505                 510                 515

ATT TGC TGG TCA GGA GAC TTT CAA GAA AGA CCA CAG TCT GCA AAG ACC     1638
Ile Cys Trp Ser Gly Asp Phe Gln Glu Arg Pro Gln Ser Ala Lys Thr
                520                 525                 530
```

-continued

```
AGG TTC TGG AAA AAC TTA AGA TAC CAG ATG CCA GCC CAA CGG AGA TCA    1686
Arg Phe Trp Lys Asn Leu Arg Tyr Gln Met Pro Ala Gln Arg Arg Ser
            535                 540                 545

CCA TTG TCT AAA CAC CGC TTA CTA ACC CTG GAT CCT GTG CGG GAC ACT    1734
Pro Leu Ser Lys His Arg Leu Leu Thr Leu Asp Pro Val Arg Asp Thr
            550                 555                 560

AAG GAG AAA CTG CCG GCA GCA ACA CAC TTA CCA CTC GGC TAGCATGGC      1782
Lys Glu Lys Leu Pro Ala Ala Thr His Leu Pro Leu Gly
            565                 570             575
```

(2) INFORMATION FOR SEQ ID NO:4:

(i) SEQUENCE CHARACTERISTICS:
        (A) LENGTH: 576 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Asn Met Lys Val Leu Leu Gly Leu Ile Cys Leu Met Val Pro
 1               5                  10                  15

Leu Leu Ser Leu Glu Ile Asp Val Cys Thr Glu Tyr Pro Asn Gln Ile
            20                  25                  30

Val Leu Phe Leu Ser Val Asn Glu Ile Asp Ile Arg Lys Cys Pro Leu
        35                  40                  45

Thr Pro Asn Lys Met His Gly Asp Thr Ile Ile Trp Tyr Lys Asn Asp
    50                  55                  60

Ser Lys Thr Pro Ile Ser Ala Asp Arg Asp Ser Arg Ile His Gln Gln
65                  70                  75                  80

Asn Glu His Leu Trp Phe Val Pro Ala Lys Val Glu Asp Ser Gly Tyr
                85                  90                  95

Tyr Tyr Cys Ile Val Arg Asn Ser Thr Tyr Cys Leu Lys Thr Lys Val
            100                 105                 110

Thr Val Thr Val Leu Glu Asn Asp Pro Gly Leu Cys Tyr Ser Thr Gln
        115                 120                 125

Ala Thr Phe Pro Gln Arg Leu His Ile Ala Gly Asp Gly Ser Leu Val
    130                 135                 140

Cys Pro Tyr Val Ser Tyr Phe Lys Asp Glu Asn Asn Glu Leu Pro Glu
145                 150                 155                 160

Val Gln Trp Tyr Lys Asn Cys Lys Pro Leu Leu Leu Asp Asn Val Ser
                165                 170                 175

Phe Phe Gly Val Lys Asp Lys Leu Leu Val Arg Asn Val Ala Glu Glu
            180                 185                 190

His Arg Gly Asp Tyr Ile Cys Arg Met Ser Tyr Thr Phe Arg Gly Lys
        195                 200                 205

Gln Tyr Pro Val Thr Arg Val Ile Gln Phe Ile Thr Ile Asp Glu Asn
    210                 215                 220

Lys Arg Asp Arg Pro Val Ile Leu Ser Pro Arg Asn Glu Thr Ile Glu
225                 230                 235                 240

Ala Asp Pro Gly Ser Met Ile Gln Leu Ile Cys Asn Val Thr Gly Gln
                245                 250                 255

Phe Ser Asp Leu Val Tyr Trp Lys Trp Asn Gly Ser Glu Ile Glu Trp
            260                 265                 270

Asn Asp Pro Phe Leu Ala Glu Asp Tyr Gln Phe Val Glu His Pro Ser
        275                 280                 285
```

```
Thr Lys Arg Lys Tyr Thr Leu Ile Thr Thr Leu Asn Ile Ser Glu Val
    290                 295                 300

Lys Ser Gln Phe Tyr Arg Tyr Pro Phe Ile Cys Val Val Lys Asn Thr
305                 310                 315                 320

Asn Ile Phe Glu Ser Ala His Val Gln Leu Ile Tyr Pro Val Pro Asp
                325                 330                 335

Phe Lys Asn Tyr Leu Ile Gly Gly Phe Ile Ile Leu Thr Ala Thr Ile
                340                 345                 350

Val Cys Cys Val Cys Ile Tyr Lys Val Phe Lys Val Asp Ile Val Leu
                355                 360                 365

Trp Tyr Arg Asp Ser Cys Ser Gly Phe Leu Pro Ser Lys Ala Ser Asp
    370                 375                 380

Gly Lys Thr Tyr Asp Ala Tyr Ile Leu Tyr Pro Lys Thr Leu Gly Glu
385                 390                 395                 400

Gly Ser Phe Ser Asp Leu Asp Thr Phe Val Phe Lys Leu Leu Pro Glu
                405                 410                 415

Val Leu Glu Gly Gln Phe Gly Tyr Lys Leu Phe Ile Tyr Gly Arg Asp
                420                 425                 430

Asp Tyr Val Gly Glu Asp Thr Ile Glu Val Thr Asn Glu Asn Val Lys
    435                 440                 445

Lys Ser Arg Arg Leu Ile Ile Ile Leu Val Arg Asp Met Gly Gly Phe
450                 455                 460

Ser Trp Leu Gly Gln Ser Ser Glu Glu Gln Ile Ala Ile Tyr Asn Ala
465                 470                 475                 480

Leu Ile Gln Glu Gly Ile Lys Ile Val Leu Leu Glu Leu Glu Lys Ile
                485                 490                 495

Gln Asp Tyr Glu Lys Met Pro Asp Ser Ile Gln Phe Ile Lys Gln Lys
                500                 505                 510

His Gly Val Ile Cys Trp Ser Gly Asp Phe Gln Glu Arg Pro Gln Ser
                515                 520                 525

Ala Lys Thr Arg Phe Trp Lys Asn Leu Arg Tyr Gln Met Pro Ala Gln
    530                 535                 540

Arg Arg Ser Pro Leu Ser Lys His Arg Leu Leu Thr Leu Asp Pro Val
545                 550                 555                 560

Arg Asp Thr Lys Glu Lys Leu Pro Ala Ala Thr His Leu Pro Leu Gly
                565                 570                 575

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Primer oligonucleotide (iii) HYPOTHETICAL: NO (iv) ANTI-SENSE: NO (vii) IMMEDIATE SOURCE:
        (B) CLONE: Primer Oligonuleotide to 5' Leader Sequence of IL-1
            Receptor (xi) SEQUENCE DESCRIPTION: SEQ ID NO:5:

GCGGATCCCC TCCTGAGAAG CT                                              22

(2) INFORMATION FOR SEQ ID NO:6:
```

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Primer oligonucleotide (iii) HYPOTHETICAL: NO (iv) ANTI-SENSE: NO (vii) IMMEDIATE SOURCE:
        (B) CLONE: Primer Oligonucleotide Upstream of Transmembrane
            Portion of IL-1 Receptor (xi) SEQUENCE DESCRIPTION: SEQ ID NO:6:

GCGGATCCCA TGTGCTACTG G                                              21
```

VIRAL VECTORS TO INHIBIT LEUKOCYTE INFILTRATION OR CARTILAGE DEGRADATION OF JOINTS

CROSS-REFERENCE TO RELATED APPLICATION

This application is a continuation of Ser. No. 08/027,750 filed Mar. 8, 1993, now abandoned, which is a continuation-in-part of Ser. No. 07/963,928, filed Oct. 20, 1992, now abandoned, which is a continuation of Ser. No. 07/630,981, filed Dec. 20, 1990 abandoned.

BACKGROUND OF THE INVENTION

1. Field of the Invention

The present invention relates to a method of introducing at least one gene encoding a product into at least one cell of a connective tissue of a mammalian host for use in treating the mammalian host. This method discloses employing DNA vector molecules containing a gene encoding the product and infecting the connective tissue cells of the mammalian host using the DNA vector molecule. This invention provides a method of introducing at least one gene encoding a product into at least one cell of a connective tissue of a mammalian host for use in treating the mammalian host including employing non-viral means for effecting such introduction.

The present invention also relates to a method to produce an animal model for the study of connective tissue pathology.

The present invention further relates to a method of using a gene encoding a truncated interleukin-1 receptor to resist the deleterious pathological changes associated with arthritis. More specifically, this invention provides a method wherein a gene coding for an extracellular interleukin-1 binding domain of an interleukin-1 receptor is introduced into synovial cells of a mammalian host in vivo for neutralizing the destructive activity of interleukin-1 upon cartilage and other soft tissues. As an alternative, the patients own synovial cells are transduced in vitro and introduced back into the affected joint, using transplantation procedures such as for example, intra-articular injection.

As an alternative to the in vitro manipulation of synovia, the gene encoding the product of interest is introduced into liposomes and injected directly into the area of the joint, where the liposomes fuse with synovial cells, resulting in an in vivo gene transfer to synovial tissue. As an additional alternative to the in vitro manipulation of synovia, the gene encoding the product of interest is introduced into the area of the joint as naked DNA. The naked DNA enters the synovial cell, resulting in an in vivo gene transfer to synovial tissue.

As an another alternative, hematopoietic progenitor cells or the mature lymphoid or myeloid cells may be transfected in vitro, recovered and injected into the bone marrow of the patient using techniques known to the skilled artisan.

2. Brief Description of the Related Art

Arthritis involves inflammation of a joint that is usually accompanied by pain and frequently changes in structure. Arthritis may result from or be associated with a number of conditions including infection, immunological disturbances, trauma and degenerative joint diseases such as, for example, osteoarthritis. The biochemistry of cartilage degradation in joints and cellular changes have received considerable investigation.

In a healthy joint, cells in cartilage (chondrocytes) and the surrounding synovium (synoviocytes) are in a resting state. In this resting state, these cells secrete basal levels of prostaglandin $E_2$ and various neutral proteinases, such as, for example, collagenase, gelatinase and stromelysin, with the ability to degrade cartilage. During the development of an arthritic condition, these cells become activated. In the activated state, synoviocytes and chondrocytes synthesize and secrete large amounts of prostaglandin $E_2$ and neutral proteinases.

In efforts to identify pathophysiologically relevant cell activators, it has been known that the cytokine interleukin-1 activates chondrocytes and synoviocytes and induces cartilage breakdown in vitro and in vivo. Additionally, interleukin-1 is a growth factor for synoviocytes and promotes their synthesis of matrix, two properties suggesting the involvement of interleukin-1 in the synovial hypertrophy that accompanies arthritis. In contrast, interleukin-1 inhibits cartilaginous matrix synthesis by chondrocytes, thereby suppressing repair of cartilage. Interleukin-1 also induces bone resorption and thus may account for the loss of bone density seen in rheumatoid arthritis. Interleukin-1 is inflammatory, serves as a growth factor for lymphocytes, is a chemotactic factor and a possible activator of polymorphonuclear leukocytes (PMNs). When present in a sufficient concentration, interleukin-1 may cause fever, muscle wasting and sleepiness.

The major source of interleukin-1 in the joint is the synovium. Interleukin-1 is secreted by the resident synoviocytes, which are joined under inflammatory conditions by macrophages and other white blood cells.

Much attention has been devoted to the development of a class of agents identified as the "Non-Steroidal Anti-Inflammatory Drugs" (hereinafter "NSAIDs"). The NSAIDs inhibit cartilage synthesis and repair and control inflammation. The mechanism of action of the NSAIDs appears to be associated principally with the inhibition of prostaglandin synthesis in body tissues. Most of this development has involved the synthesis of better inhibitors of cyclo-oxygenase, a key enzyme that catalyzes the formation of prostaglandin precursors (endoperoxides) from arachidonic acid. The anti-inflammatory effect of the NSAIDs is thought to be due in part to inhibition of prostaglandin synthesis and release during inflammation. Prostaglandins are also believed to play a role in modulating the rate and extent of leukocyte infiltration during inflammation. The NSAIDs include, such as, for example, acetylsalicylic acid (aspirin), fenoprofen calcium (Nalfon® Pulvules®, Dista Products Company), ibuprofen (Motrin®, The Upjohn Company), and indomethacin (Indocin®, Merck, Sharp & Dohme).

In contrast, the studies upon which the present invention is based show that production of the various neutral proteinases with the ability to degrade cartilage occurs even if prostaglandin synthesis is completely blocked.

Therapeutic intervention in arthritis is hindered by the inability to target drugs, such as the NSAIDs, to specific areas within a mammalian host, such as, for example a joint. Traditional routes of drug delivery, such as for example, oral, intravenous or intramuscular administration, depend upon vascular perfusion of the synovium to carry the drug to the joint. This is inefficient because transynovial transfer of small molecules from the synovial capillaries to the joint space occurs generally by passive diffusion. This diffusion is less efficient with increased size of the target molecule. Thus, the access of large drug molecules, for example, proteins, to the joint space is substantially restricted. Intra-articular injection of drugs circumvents those limitations; however, the half-life of drugs administered intra-articularly is generally short. Another disadvantage of intra-articular injection of drugs is that frequent repeated injections are necessary to obtain acceptable drug levels at the joint spaces for treating a chronic condition such as, for example, arthritis. Because therapeutic agents heretofore could not be selectively targeted to joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side effects, such as for example, gastrointestinal upset and changes in the hemato-logical, cardiovascular, hepatic and renal systems of the mammalian host.

It has been shown that genetic material can be introduced into mammalian cells by chemical or biologic means. Moreover, the introduced genetic material can be expressed so that high levels of a specific protein can be synthesized by the host cell. Cells retaining the introduced genetic material may include an antibiotic resistance gene thus providing a selectable marker for preferential growth of the transduced cell in the presence of the corresponding antibiotic. Chemical compounds for inhibiting the production of interleukin-1 are also known.

U.S. Pat. No. 4,778,806 discloses a method of inhibiting the production of interleukin-1 by monocytes and/or macrophages in a human by administering through the parenteral route a 2-2'-[1,3-propan-2-onediyl-bis (thio)] bis-1 H-imidazole or a pharmaceutically acceptable salt thereof. This patent discloses a chemical compound for inhibiting the production of interleukin-1. By contrast, in one embodiment of the present invention, gene therapy is employed that is capable of binding to and neutralizing interleukin-1.

U.S. Pat. No. 4,780,470 discloses a method of inhibiting the production of interleukin-1 by monocytes in a human by administering a 4,5-diaryl-2 (substituted) imidazole. This patent also discloses a chemical compound for inhibiting the production of interleukin-1.

U.S. Pat. No. 4,794,114 discloses a method of inhibiting the 5-lipoxygenase pathway in a human by administering a diaryl-substituted imidazole fused to a thiazole, pyrrolidine or piperidine ring or a pharmaceutically acceptable salt thereof. This patent also discloses a chemical compound for inhibiting the production of interleukin-1.

U.S. Pat. No. 4,870,101 discloses a method for inhibiting the release of interleukin-1 and for alleviating interleukin-1 mediated conditions by administering an effective amount of a pharmaceutically acceptable anti-oxidant compound such as disulfiram, tetrakis [3-(2,6-di-tert-butyl-4-hydroxyphenyl) propionyloxy methyl] methane or 2,4-di-isobutyl-6-(N,N-dimethylamino methyl)-phenol. This patent discloses a chemical compound for inhibiting the release of interleukin-1.

U.S. Pat. No. 4,816,436 discloses a process for the use of interleukin-1 as an anti-arthritic agent. This patent states that interleukin-1, in association with a pharmaceutical carrier, may be administered by intra-articular injection for the treatment of arthritis or inflammation. In contrast, the present invention discloses a method of using and preparing a gene that is capable of binding to and neutralizing interleukin-1 as a method of resisting arthritis.

U.S. Pat. No. 4,935,343 discloses an immunoassay method for the detection of interleukin-1 beta that employs a monoclonal antibody that binds to interleukin-1 beta but does not bind to interleukin-1 beta. This patent discloses that the monoclonal antibody binds to interleukin-1 beta and blocks the binding of interleukin-1 beta to interleukin-1 receptors, and thus blocking the biological activity of interleukin-1 beta. The monoclonal antibody disclosed in this patent may be obtained by production of an immunogen through genetic engineering using recombinant DNA technology. The immunogen is injected into a mouse and thereafter spleen cells of the mouse are immortalized by fusing the spleen cells with myeloma cells. The resulting cells include the hybrid continuous cell lines (hybridomas) that may be later screened for monoclonal antibodies. This patent states that the monoclonal antibodies of the invention may be used therapeutically, such as for example, in the immunization of a patient, or the monoclonal antibodies may be bound to a toxin to form an immunotoxin or to a radioactive material or drug to form a radio pharmaceutical or pharmaceutical.

U.S. Pat. No. 4,766,069 discloses a recombinant DNA cloning vehicle having a DNA sequence comprising the human interleukin-1 gene DNA sequence. This patent provides a process for preparing human interleukin-1 beta, and recovering the human interleukin-1 beta. This patent discloses use of interleukin-1 as an immunological reagent in humans because of its ability to stimulate T-cells and B-cells and increase immunoglobulin synthesis.

U.S. Pat. No. 4,396,601 discloses a method for providing mammalian hosts with additional genetic capability. This patent provides that host cells capable of regeneration are removed from the host and treated with genetic material including at least one marker which allows for selective advantage for the host cells in which the genetic material is capable of expression and replication. This patent states that the modified host cells are then returned to the host under regenerative conditions. In the present invention, genetic material may be directly introduced (a) into host cells in vivo or (b) into synoviocytes in vitro for subsequent transplantation back into the patient's joints.

U.S. Pat. No. 4,968,607 discloses a DNA sequence encoding a mammalian interleukin-1 receptor protein which exhibits interleukin-1 binding activity.

In spite of these prior art disclosures, there remains a very real and substantial need for a method of introducing at least one gene encoding a product into at least one cell of a connective tissue of a mammalian host in vitro, or alternatively in vivo, for use in treating the mammalian host. Further, there is a need for a process wherein a gene encoding a truncated interleukin-1 receptor is used to resist the deleterious pathological changes associated with arthritis. More specifically there is a need for such a process where a gene coding for the extracellular interleukin-1 binding domain of the interleukin-1 receptor, capable of binding to and neutralizing interleukin-1 is expressed in host synovial cells in vivo.

SUMMARY OF THE INVENTION

The present invention has met the hereinbefore described need. A method of introducing at least one gene encoding a product into at least one cell of a connective tissue of a mammalian host for use in treating the mammalian host is provided for in the present invention. This method includes employing recombinant techniques to produce a DNA vector molecule containing the gene encoding for the product and infecting the connective tissue cell of the mammalian host using the DNA vector molecule containing the gene coding for the product. The DNA vector molecule can be any DNA molecule capable of being delivered and maintained within the target cell or tissue such that the gene encoding the product of interest can be stably expressed. The DNA vector molecule preferably utilized in the present invention is either a viral DNA vector molecule or a plasmid DNA viral molecule. This method preferably includes introducing the gene encoding the product into the cell of the mammalian connective tissue for a therapeutic use.

More specifically, this method includes employing as the gene a gene capable of encoding at least one of the materials which is selected from the group which includes (a) a human interleukin-1 receptor antagonist protein or a biologically active derivative or fragment thereof, (b) a Lac Z marker gene capable of encoding a beta-galactosidase protein or a biologically active derivative or fragment thereof, (c) a soluble interleukin-1 receptor protein or a biologically active derivative or fragment thereof, (d) a proteinase inhibitor, and (e) a cytokine, and employing as the viral vector at least one vector which is selected from the group which includes (a) a retroviral vector including at least one of the materials selected from the group which includes MFG and BAG, (b) an adeno-associated virus, (c) an adenovirus, and (d) a herpes virus, including but not limited to herpes simplex 1 or herpes simplex 2.

A further embodiment of the present invention includes employing as the gene a gene capable of encoding at least one of the materials which is selected from the group which includes (a) a human interleukin-1 receptor antagonist protein or a biologically active derivative or fragment thereof, (b) a Lac Z marker gene capable of encoding a beta-galactosidase protein or a biologically active derivative or fragment thereof, (c) a soluble interleukin-1 receptor protein or a biologically active derivative or fragment thereof, (d) a proteinase inhibitor, and (e) a cytokine, and employing as the DNA plasmid vector any DNA plasmid vector known to one of ordinary skill in the art capable of stable maintenance within the targeted cell or tissue upon delivery, regardless of the method of delivery utilized. One such method is the direct delivery of the DNA vector molecule, whether it be a viral or plasmid DNA vector molecule, to the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a proteinase inhibitor and (e) a cytokine. In a specific method disclosed as an example, and not as a limitation to the present invention, a DNA plasmid vector containing the interleukin-1 beta coding sequence was ligated downstream of the cytomegalovirus (CMV) promoter. This DNA plasmid construction was encapsulated within liposomes and injected intra-articularly into the knee joints of recipient rabbits. Interleukin-1 beta was expressed and significant amounts of interleukin-1 beta was recovered from the synovial tissue. An alternative is injection of the naked plasmid DNA into the knee joint, allowing direct transfection of the DNA into the synovial tissue.

Another embodiment of this invention provides a method for introducing at least one gene encoding a product into at least one cell of a connective tissue of a mammalian host for use in treating the mammalian host. This method includes employing non-viral means for introducing the gene encoding for the product into the connective tissue cell. More specifically, this method includes employing non-viral means which is selected from at least one of the group which includes (a) at least one liposome, (b) $Ca_3(PO_4)_2$, (c) electroporation, and (d) DEAE-dextran, and includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a proteinase inhibitor (e) a soluble tumor necrosis factor receptor protein or biologically active derivative or fragment thereof, and (f) a cytokine.

A further embodiment of this invention provides an additional method for introducing at least one gene encoding a product into at least one cell of a connective tissue of a mammalian host for use in treating the mammalian host. This additional method includes employing the biologic means of utilizing a virus to deliver the DNA vector molecule to the target cell or tissue. Preferably, the virus is a psuedovirus, the genome having been altered such that the psuedovirus is capable only of delivery and stable maintenance within the target cell; but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a proteinase inhibitor and (e) a cytokine.

A further embodiment of this invention includes a method to produce an animal model for the study of connective tissue pathology which includes introducing at least one gene encoding a product into at least one cell of a connective tissue of a mammalian host.

Another embodiment of this invention provides a method of using the gene encoding an extracellular interleukin-1 binding domain of the interleukin-1 receptor. This gene is capable of binding to and neutralizing interleukin-1 in vivo to substantially resist the degradation of cartilage in a mammalian host. Unlike previous pharmacological efforts, the method of this invention employs gene therapy in vivo to address the chronic debilitating effects of arthritis.

A preferred method of using the gene coding for the truncated interleukin-1 receptor of this invention involves employing recombinant techniques to generate a cell line which produces infectious retroviral particles containing the gene coding for the truncated interleukin-1 receptor. The producer cell line is generated by inserting the gene coding into a retroviral vector under the regulation of a suitable eukaryotic promoter, transfecting the retroviral vector containing the gene coding into the retroviral packaging cell line for the production of a viral particle that is capable of expressing the gene coding for the truncated interleukin-1 receptor, and infecting the synovial cells of a mammalian host using the viral particle.

More specifically, the method of using the hereinbefore described gene coding for the truncated interleukin-1 receptor involves introducing the viral particles obtained from the retroviral packaging cell line directly by intra-articular injection into a joint space of a mammalian host that is lined with synovial cells. In a preferred embodiment, synoviocytes recovered from the knee joint are cultured in vitro for subsequent utilization as a delivery system for gene therapy. It will be apparent that Applicants are not limited to the use of the specific synovial tissue disclosed. It would be possible to utilize other tissue sources, such as skin cells, for in vitro culture techniques. The method of using the gene of this invention may be employed both prophylactically and in the therapeutic treatment of arthritis. It will also be apparent that Applicants are not limited to prophylactic or therapeutic applications in treating only the knee joint. It would be possible to utilize the present invention either prophylactically or therapeutically to treat arthritis in any susceptible joint.

In another embodiment of this invention, a method of using the hereinbefore described gene coding for the truncated interleukin-1 receptor involves infecting synovial cells in culture with the viral particles and subsequently transplanting the infected synovial cells back into the joint. This method of using the gene of this invention may also be employed prophylactically and in the therapeutic treatment of arthritis in any area susceptible to the disorder.

In another embodiment of this invention, a method of using the gene coding for an extracellular interleukin-1 binding domain of the interleukin-1 receptor that is capable of binding to and neutralizing interleukin-1 includes employing recombinant techniques to produce a retrovirus vector carrying two genes. The first gene encodes the extracellular interleukin-1 binding domain of the interleukin receptor, and the second gene encodes for selectable antibiotic resistance. This method of use involves transfecting the retrovirus vector into a retrovirus packaging cell line to obtain a cell line producing infectious retroviral particles carrying the gene.

Another embodiment of this invention provides a method of preparing a gene encoding an extracellular interleukin-1 binding domain of the interleukin-1 receptor including synthesizing the gene by a polymerase chain reaction, introducing the amplified interleukin-1 receptor coding sequence into a retroviral vector, transfecting the retroviral vector into a retrovirus packaging cell line and collecting viral particles from the retrovirus packaging cell line.

In another embodiment of this invention, a compound for parenteral administration to a patient in a therapeutically effective amount is provided for that contains a gene encoding an extracellular interleukin-1 binding domain of the interleukin-1 receptor and a suitable pharmaceutical carrier.

Another embodiment of this invention provides for a compound for parenteral administration to a patient in a prophylactically effective amount that includes a gene encoding an extracellular interleukin-1 binding domain of the interleukin-1 receptor and a suitable pharmaceutical carrier.

An additional embodiment of the invention involves transfection of hematopoietic progenitor cells or mature lymphoid or myeloid cells with a DNA vector molecule containing any of the gene or genes disclosed throughout the specification. The transfected cells are recovered and injected into the bone marrow of the patient using techniques known and available to one of ordinary skill in the art. It will be possible, within the scope of this method, to use cells derived from donor bone marrow instead of cells derived from recipient bone marrow so as to modify rejection.

In another embodiment of the invention, synoviocytes are transfected in vivo subsequent to direct intra-articular injection of a DNA molecule containing the gene of interest into the joint. Transfection of the recipient synovial cells bypasses the requirement of removal, culturing, in vitro transfection, selection and transplanting the DNA vector containing—synoviocytes (as disclosed in the Example section) to promote stable expression of the heterologous gene of interest. Methods of injecting the DNA molecule into the joint includes, but is not limited to, encapsulation of the DNA molecule into cationic liposomes or the direct injection of the DNA molecule itself into the joint. The DNA molecule, regardless of the form of presentation to the knee joint, is preferably presented as a DNA vector molecule, either as viral DNA vector molecule, or preferably, a DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the synovial tissue.

It is an object of the present invention to provide a method of introducing at least one gene encoding a product into at least one cell of a connective tissue of a mammalian host for use in treating the mammalian host.

It is an object of the invention to provide a method of introducing a gene encoding a product into at least one cell of a connective tissue of a mammalian host for a therapeutic use.

It is an object of the present invention to provide a method of introducing into the synovial lining cells of a mammalian arthritic joint at least one gene which codes for proteins having therapeutic properties.

It is an object of the present invention to provide an animal model for the study of connective tissue pathology.

It is an object of the present invention to provide a method of using in vivo a gene coding for the extracellular interleukin-1 binding domain of the interleukin-1 receptor that is capable of binding to and neutralizing substantially all isoforms of interleukin-1, including interleukin-1 alpha and interleukin-1 beta.

It is an object of the present invention to provide a method of using a gene in vivo in a mammalian host that is capable of binding to and neutralizing substantially all isoforms of interleukin-1 and thus, substantially resist the degradation of cartilage and protect surrounding soft tissues of the joint space.

It is an object of the present invention to provide a method of using in vivo a gene coding for the extracellular interleukin-1 binding domain of the interleukin-1 receptor that is capable of binding to and neutralizing substantially all isoforms of interleukin-1 for the prevention of arthritis in patients that demonstrate a high susceptibility for developing the disease.

It is an object of the present invention to provide a method of using in vivo a gene coding for an extracellular interleukin-1 binding domain of an interleukin-1 receptor that is capable of binding to and neutralizing substantially all isoforms of interleukin-1 for the treatment of patients with arthritis.

It is an object of the present invention to provide a method of using in vivo a gene or genes that address the chronic debilitating pathophysiology of arthritis.

It is a further object of the present invention to provide a compound for parenteral administration to a patient which comprises a gene encoding an extracellular interleukin-1 binding domain of the interleukin-1 receptor and a suitable pharmaceutical carrier.

These and other objects of the invention will be more fully understood from the following description of the invention, the referenced drawings attached hereto and the claims appended hereto.

BRIEF DESCRIPTION OF THE DRAWINGS

FIG. 5 shows data demonstrating the inhibition of chondrocytes by the addition of medium conditioned by MFG-IRAP infected HIG-82 cells.

FIGS. 8A–8C show the amino acid and nucleotide sequence of the human (SEQ ID NOS: 1–2) and mouse (SEQ ID NOS: 3–4) interleukin-1 receptors.

DETAILED DESCRIPTION OF THE INVENTION

Figure 1:
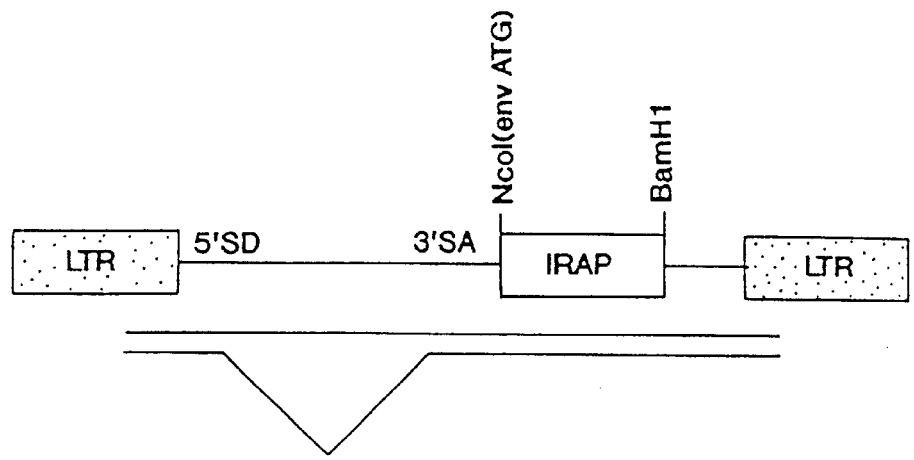
FIG. 1 shows the structure of the cDNA encoding the human interleukin-1 receptor antagonist protein (IRAP) gene inserted into the NcoI and BamHI cloning sites of the retroviral vector MFG.

As used herein, the term "patient" includes members of the animal kingdom including but not limited to human beings.

As used herein, the term "mammalian host" includes members of the animal kingdom including but not limited to human beings.

As used herein, the term "connective tissue" includes but is not limited to a ligament, a cartilage, a tendon, and a synovium of a mammalian host.

As used herein, the term "DC-chol" means a cationic liposome containing cationic cholesterol derivatives. The "DC-chol" molecule includes a tertiary amino group, a medium length spacer arm (two atoms) and a carbamyol linker bond as described in *Biochem. Biophys. Res. Commun.*, 179:280–285 (1991), X. Gao and L. Huang.

As used herein, "SF-chol" is defined as a type of cationic liposome.

As used herein, the term "biologically active" used in relation to liposomes denotes the ability to introduce functional DNA and/or proteins into the target cell.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

Connective tissues are difficult organs to target therapeutically. Intravenous and oral routes of drug delivery that are known in the art provide poor access to these connective tissues and have the disadvantage of exposing the mammalian host body systemically to the therapeutic agent. More specifically, known intra-articular injection of joints provides direct access to a joint. However, most of the injected drugs have a short intra-articular half-life. The present invention solves these problems by introducing into the connective tissue of a mammalian host genes encoding for proteins that may be used to treat the mammalian host. More specifically, this invention provides a method for introducing into the connective tissue of a mammalian host genes encoding for proteins with anti-arthritic properties.

The present invention provides a method of introducing at least one gene encoding a product into at least one cell of a connective tissue of a mammalian host for use in treating the mammalian host which comprises employing recombinant techniques to produce a viral vector which contains the gene encoding for the product, and infecting the connective tissue cell of the mammalian host using the viral vector containing the gene coding for the product. This method preferably includes introducing the gene encoding the product into at least one cell of the connective tissue of the mammalian host for a therapeutic use.

In one embodiment of this invention, the method as hereinbefore described includes employing as the gene a gene capable of encoding a human interleukin-1 receptor antagonist protein (IRAP).

In another embodiment of this invention, the method as hereinbefore described includes employing as the gene a Lac Z marker gene capable of encoding a beta-galactosidase.

In another embodiment of this invention, the method as hereinbefore described includes employing as the gene a gene capable of encoding a soluble interleukin-1 receptor.

Another embodiment of this invention includes the method as hereinbefore described including employing as the gene a gene capable of encoding at least proteinase inhibitor. More specifically, this method preferably includes employing a tissue inhibitor of a metalloproteinases as the proteinase inhibitor.

Another embodiment of this invention includes the method as hereinbefore described including employing as the gene a gene capable of encoding at least one cytokine. More specifically, this method includes employing as the cytokine at least one material selected from the group consisting of interleukin-1 alpha, interleukin-1 beta, interleukin-2, interleukin-3, interleukin-4, interleukin-5, interleukin-6, interleukin-7, interleukin-8, interleukin-9, interleukin-10, interleukin-11, interleukin-12, tumor necrosis factor $\alpha$, and tumor necrosis factor $\beta$.

A further embodiment of this invention includes a method as hereinbefore described including employing as the cytokine at least one transforming growth factor. More specifically, this method includes employing as the transforming growth factor a growth factor selected from the group consisting of TGF-beta$_1$, TGF-beta$_2$, TGF-beta$_3$, and TGF-alpha. Each transforming growth factor is commercially available from R & D Systems, 614 McKinley Place, N.E., Minneapolis, Minn. 55413.

In another embodiment of this invention, the method as hereinbefore described includes employing as the cytokine at least one fibroblast growth factor. The fibroblast growth factors are also commercially available from R & D Systems, 614 McKinley Place, N.E., Minneapolis, Minn. 55413.

Another embodiment of this invention includes the method as hereinbefore described including employing as the viral vector a retroviral vector. More specifically, this method includes employing as the retroviral vector at least one material selected from the group consisting of MFG and BAG. A preferred embodiment of this invention includes providing the method as hereinbefore described including employing as the gene a gene capable of encoding a human interleukin-1 receptor antagonist protein and employing MFG as the retroviral vector.

Another preferred embodiment of this invention includes the method as hereinbefore described including employing a Lac Z marker gene as the gene capable of encoding a beta-galactosidase and employing MFG as the retroviral vector.

Another preferred embodiment of this invention provides the method as hereinbefore described including employing a Lac Z neo marker gene as the gene capable of encoding a beta-galactosidase and employing BAG as the retroviral vector.

In a most preferred embodiment of this invention, the method as hereinbefore described includes employing a retroviral vector selected from the group consisting of MFG and BAG and includes employing as the gene a gene capable of encoding a soluble interleukin-1 receptor.

In another embodiment of this invention, a method as hereinbefore described is provided including employing as the gene a gene capable of encoding at least one proteinase inhibitor and including employing as the retroviral vector at least one material selected from the group consisting of MFG and BAG.

In another embodiment of this invention, a method as hereinbefore described is provided which includes employing as the retroviral vector at least one material selected from the group consisting of MFG and BAG and including employing as the gene a gene capable of encoding at least one cytokine as hereinbefore described.

In another embodiment of this invention, a method is provided for introducing at least one gene encoding a product into at least one cell of a connective tissue of a mammalian host for use in treating the mammalian host which comprises employing recombinant techniques to produce a viral vector which contains the gene encoding for the product and infecting the connective tissue cell of the mammalian host using the viral vector containing the gene coding for the product, wherein the viral vector is at least one vector selected from the group consisting of an adeno-associated virus, an adenovirus, and a herpes virus, such as herpes simplex type-1 or herpes simplex type-2. This method includes employing as the gene a gene capable of encoding at least one material selected from the group which includes (a) a human interleukin-1 receptor antagonist protein, (b) a soluble interleukin-1 receptor, (c) a Lac Z marker gene capable of encoding a beta-galactosidase, (d) at least one proteinase inhibitor and (e) at least one cytokine.

More specifically, this method includes employing a tissue inhibitor of metalloproteinases as the proteinase inhibitor and includes employing as the cytokine at least one of the materials selected from the group which includes (a) at least one transforming growth factor selected from the group consisting of TGF-beta$_1$, TGF-beta$_2$, TGF-beta$_3$, and TGF-alpha, (b) at least one fibroblast growth factor, (c) interleukin-1 alpha, (d) interleukin-1 beta, (e) interleukin-2, (f) interleukin-3, (g) interleukin-4, (h) interleukin-5, (i) interleukin-6, (j) interleukin-7, (k) interleukin-8, (l) interleukin-9, (m) interleukin-10, (n) interleukin-11, and (o) interleukin-12 (p) tumor necrosis factor $\alpha$, and (q) tumor necrosis factor $\beta$.

Another embodiment of this invention includes the method as hereinbefore described including introducing the gene into a connective tissue which tissue is selected from the group consisting of a ligament, a cartilage, a tendon, and a synovium. It is preferable that this method includes employing a cruciate ligament as the ligament. Most preferable this method includes employing as the cruciate ligament a ligament selected from the group consisting of an anterior cruciate ligament and a posterior cruciate ligament.

Another embodiment of this invention includes the method as hereinbefore described including employing as the gene a gene having DNA that is capable of maintenance and expression.

A further embodiment of this invention includes the method as hereinbefore described including introducing the gene into the cell in vitro. This method includes subsequently transplanting the infected cell into the mammalian host. This method also includes after effecting the infecting of the connective tissue cell but before the transplanting of the infected cell into the mammalian host, storing the infected connective tissue cell. It will be appreciated by those skilled in the art that the infected connective tissue cell may be stored frozen in 10 percent DMSO in liquid nitrogen. This method includes employing a method to substantially prevent the development of arthritis in a mammalian host having a high susceptibility of developing arthritis.

The method of this invention includes employing the method on an arthritic mammalian host for a therapeutic use. This method includes employing a method to repair and regenerate the connective tissue which tissue is selected from the group consisting of a ligament, a cartilage, a tendon, and a synovium. This method includes employing the method on a mammalian host that is a human being.

Another embodiment of this invention includes a method of introducing at least one gene encoding a product into at least one cell of a connective tissue of a mammalian host for use in treating the mammalian host as hereinbefore described including effecting in vivo the infection of the cell by introducing the viral vector containing the gene coding for the product directly into the mammalian host. Preferably, this method includes effecting the direct introduction into the mammalian host by intra-articular injection. This method includes employing the method to substantially prevent a development of arthritis in a mammalian host having a high susceptibility of developing arthritis. This method also includes employing the method on an arthritic mammalian host for therapeutic use. Further this method as includes employing the method to repair and regenerate the connective tissue as hereinbefore defined.

In yet another embodiment of this invention, a method of introducing at least one gene encoding a product into at least one cell of a connective tissue of a mammalian host for use in treating the mammalian host includes employing non-viral means for introducing the gene encoding for the product into the connective tissue cell. This method includes employing non-viral means selected from the group consisting of at least one liposome, $Ca_3(PO_4)_2$, electroporation, and DEAE-dextran. This method includes employing as the liposome a material selected from the group consisting of DC-chol and SF-chol.

It will be understood that the method of this invention of introducing at least one gene encoding a product into at least one cell of a connective tissue of a mammalian host for use in treating the mammalian host that includes employing non-viral means for introducing the gene encoding for the product into the connective tissue cell is a non-infectious delivery system. An advantage of the use of a non-infectious delivery system is the elimination of insertional mutagenesis and virally induced disease.

It will be appreciated by those skilled in the art, that the viral vectors employing a liposome are not limited by cell division as is required for the retroviruses to effect infection and integration of connective tissue cells. This method employing non-viral means as hereinbefore described includes employing as the gene a gene capable of encoding at least one of the following materials selected from the group which includes (a) a human interleukin-1 receptor antagonist protein, (b) a Lac Z marker gene capable of encoding a beta-galactosidase, (c) a soluble interleukin-1 receptor, (d) at least one proteinase inhibitor, (e) at least one transforming growth factor, and (f) at least one cytokine. More specifically, this method includes employing as the cytokine a cytokine selected from the group which includes interleukin-1 alpha, interleukin-1 beta, interleukin-2, interleukin-3, interleukin-4, interleukin-5, interleukin-6, interleukin-7, interleukin-8, interleukin-9, interleukin-10, interleukin-11, interleukin-12, tumor necrosis factor α, tumor necrosis factor β, at least one fibroblast growth factor, and at least one transforming growth factor. Preferably, this method includes employing as the transforming growth factor a growth factor selected from the group consisting of TGF-beta$_1$, TGF-beta$_2$, TGF-beta$_3$, and TGF-alpha.

Another preferred embodiment of this invention includes providing the method employing non-viral means as hereinbefore described which includes employing a tissue inhibitor of metalloproteinases as the proteinase inhibitor. This method employing non-viral means for introducing the gene encoding for the product into the connective tissue cell as hereinbefore described includes introducing the gene into the connective tissue which tissue is selected from the group consisting of a ligament, a cartilage, a tendon, and a synovium. Preferably, this method includes employing a cruciate ligament as the ligament. The cruciate ligament is selected from the group consisting of an anterior cruciate ligament and an posterior cruciate ligament.

Another embodiment of this invention provides the method of introducing at least one gene encoding a product into at least one cell of a connective tissue of a mammalian host for use in treating the mammalian host which includes employing non-viral means as hereinbefore described and includes employing as the gene a gene having DNA that is capable of maintenance and expression.

In yet a further embodiment of this invention, the method of introducing at least one gene encoding a product. into at least one cell of a connective tissue of a mammalian host for use in treating the mammalian host is provided that includes employing non-viral means for introducing the gene encoding for the product into the connective tissue cell in vitro and includes subsequently transplanting the cell having the gene into the mammalian host. Another embodiment of this invention provides a method including after introducing the gene encoding for the product in the connective tissue cell and before the transplanting of the connective tissue cell having the gene into the mammalian host, storing the connective tissue cell having the gene. This method includes storing connective tissue cell frozen in 10 percent DMSO in liquid nitrogen. This method includes employing a method to substantially prevent the development of arthritis in a mammalian host having a high susceptibility of developing arthritis. Further, this method includes employing the method on an arthritic mammalian host for a therapeutic use. This method includes employing the method to repair and regenerate the connective tissue which tissue is selected from the group consisting of a ligament, a cartilage, a tendon, and a synovium.

A further embodiment of this invention provides a method of introducing at least one gene encoding a product into at least one cell of a connective tissue of a mammalian host for use in treating the mammalian host which includes employing non-viral means in vivo for directly introducing the gene encoding for the product into the connective tissue cell of the mammalian host. The non-viral means is selected from the group consisting of at least one liposome, $Ca_3(PO_4)_2$ and DEAE-dextran. Preferably, this method includes effecting the in vivo introduction into the mammalian host by intra-articular injection. This method includes employing the method to substantially prevent the development of arthritis in a mammalian host having a high susceptibility of developing arthritis. Further, this method includes employing the method on an arthritic mammalian host for a therapeutic use. This method also includes employing the method to repair and regenerate the connective tissue which tissue is selected from the group consisting of a ligament, a cartilage, a tendon, and a synovium.

Another embodiment of the present invention is a method to produce an animal model for the study of connective tissue pathology. As will be understood by those skilled in the art, over-expression of interleukin-1 in the joint of a mammalian host is generally responsible for the induction of an arthritic condition. This invention provides a method for producing an animal model using the hereinbefore described gene transfer technology of this invention. Preferably, the method of this invention provides a method for producing an animal model using the hereinbefore described gene transfer technology of this invention to effect an animal model for arthritis. For example, constitutive expression of interleukin-1 in the joint of a rabbit following the method of gene transfer provided for by this invention leads to the onset of an arthritic condition. It will be appreciated by those skilled in the art that this rabbit model is suitable for use for the testing of therapeutic agents. This method includes introducing at least one gene encoding a product into at least one cell of a connective tissue of a mammalian host comprising (a) employing recombinant techniques to produce a viral vector which contains the gene encoding for the product and (b) infecting the connective tissue cell of the mammalian host using the viral vector containing the gene coding for the product for effecting the animal model. This method includes employing as the gene a material selected from the group consisting of a cytokine and a proteinase. This method includes employing as the cytokine a material selected from the group consisting of interleukin-1 alpha, interleukin-1 beta, and tumor necrosis factor-α (TNF-α). This method includes employing as the proteinase a matrix metalloproteinase. The matrix metalloproteinase is an enzyme selected from the group consisting of a collagenase, a gelatinase and a stromelysin. It will be apparent that use of the term "a collogenase, a gelatinase and a stromolysin" is meant to include the plural, and not be limited to the singular. It is well known in the art that numerous collagenases, gelatinases and stromolysins could be employed as a matrix metalloproteinase in the present invention. A further embodiment of this invention provides a method to produce an animal model for the study of connective tissue pathology which includes employing non-viral means for introducing at least one gene encoding a product into at least one cell of a connective tissue of a mammalian host for effecting the animal model. The non-viral means is selected from the group consisting of at least one liposome, $Ca_3(PO_4)_2$, electroporation, and DEAE-dextran. This method includes employing as the gene a material selected from the group consisting of a cytokine and a proteinase. This method includes employing as the cytokine a material selected from the group consisting of interleukin-1 alpha, interleukin-1 beta, and TNF-α. This method also includes employing as the proteinase a matrix metalloproteinase. The matrix metalloproteinase includes an enzyme selected from at least one of the group consisting of a collagenase, a gelatinase, and a stromelysin.

A further embodiment of the present invention includes employing as the gene a gene capable of encoding at least one of the materials which is selected from the group which includes (a) a human interleukin-1 receptor antagonist protein or a biologically active derivative or fragment thereof, (b) a Lac Z marker gene capable of encoding a beta-galactosidase protein or a biologically active derivative or fragment thereof, (c) a soluble interleukin-1 receptor protein or a biologically active derivative or fragment thereof, (d) a proteinase inhibitor, (e) a soluble tumor necrosis factor receptor protein or a biologically active derivative or fragment thereof and (f) a cytokine, and employing as the DNA vector any DNA vector, preferably a plasmid or viral vector, known to one of ordinary skill in the art capable of stable maintenance within the targeted cell or tissue upon delivery, regardless of the method of delivery utilized. In one embodiment of the invention, synoviocytes are transfected in vivo subsequent to direct intra-articular injection of a DNA molecule containing the gene of interest into the joint. Transfection of the recipient synovial cells bypasses the requirement of removal, culturing, in vitro transfection, selection and transplanting the DNA vector containing—synoviocytes (as disclosed in the Example section) to promote stable expression of the heterologous gene of interest. Methods of injecting the DNA molecule into the joint includes, but is not limited to, encapsulation of the DNA molecule into cationic liposomes or the direct injection of the DNA molecule itself into the joint. Expression of the heterologous gene of interest subsequent to in vivo transfection of the synovial tissue is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the synovial tissue. As an example, and not a limitation, of the present invention, a DNA plasmid vector containing the interleukin-1 beta coding sequence ligated downstream of the CMV promoter was encapsulated within liposomes and injected into the knee joints of recipient rabbits. Interleukin-1 beta was expressed in synovial tissue, as significant amounts of interleukin-1 beta was recovered from the synovial tissue within the region of intra-articular injection.

A further embodiment of this invention provides an additional method for introducing at least one gene encoding a product into at least one cell of a connective tissue of a mammalian host for use in treating the mammalian host. This additional method includes employing the biologic means of utilizing a virus to deliver the DNA vector molecule to the target cell or tissue. Preferably, the virus is a psuedovirus, the genome having been altered such that the psuedovirus is capable only of delivery and stable maintenance within the target cell; but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a proteinase inhibitor and (e) a soluble tumor necrosis factor receptor protein or a biologically active derivative or fragment thereof and (f) a cytokine.

The following examples are offered by way of illustration of the present invention, and not by way of limitation.

EXAMPLE I

Packaging of AAV

The only cis-acting sequences required for replication and packaging of recombinant adeno-associated virus (AAV) vector are the AAV terminal repeats. Up to 4 kb of DNA can be inserted between the terminal repeats without effecting viral replication or packaging. The virus rep proteins and viral capsid proteins are required in trans for virus replication as is an adeno-associated virus helper. To package a recombinant AAV vector, the plasmid containing the terminal repeats and the therapeutic gene is co-transfected into cells with a plasmid that expresses the rep and capsid proteins. The transfected cells are then infected with adeno-associated virus and virus isolated from the cells about 48–72 hours post-transfection. The supernatants are heated to about 56° Centigrade to inactivate the adeno-associated virus, leaving a pure virus stock of recombinant AAV.

EXAMPLE II

Electroporation

The connective tissue cells to be electroporated are placed into Hepes buffer saline (HBS) at a concentration of about $10^7$ cells per ml. The DNA to be electroporated is added at a concentration of about 5–20 ug/ml of HBS. The mixture is placed into a cuvette and inserted into the cuvette holder that accompanies the Bio-RAD electroporation device (1414 Harbour Way South, Richmond, Calif. 94804). A range between about 250 and 300 volts at a capacitance of about 960 ufarads is required for introduction of DNA into most eukaryotic cell types. Once the DNA and the cells are inserted into the Bio-RAD holder, a button is pushed and the set voltage is delivered to the cell-DNA solution. The cells are removed from the cuvette and replated on plastic dishes.

EXAMPLE III

The cDNA encoding the human interleukin-1 receptor antagonist (IRAP) was inserted into the NcoI and BamHI cloning sites of the retroviral vector MFG as shown in FIG.

1. Specifically, a Pst1 to BamHI fragment from the IRAP cDNA was linked to a synthetic oligonucleotide adapter from the NcoI site (representing the start site of translation for IRAP) to the Pst1 site (approximately 12 base pairs downstream from the NcoI site) to the MFG backbone digested at NcoI and BamHI in a three part ligation reaction. This three part ligation involving a synthetic oligo and two DNA fragments is well known by those skilled in the art of cloning. LTR means long terminal repeats, 5'SD means 5' splice donor, 3'SA means 3' splice acceptor. The straight arrow and the crooked arrow in FIG. 1 represent unspliced and spliced messenger RNAs respectively. IRAP is encoded by the spliced message.

Figure 2:
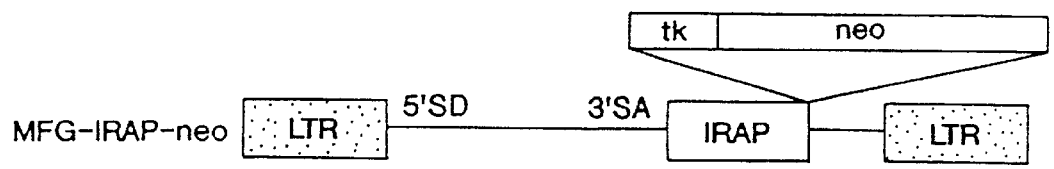
FIG. 2 shows the structure of the cDNA encoding the human interleukin-1 receptor antagonist protein (IRAP) gene with a selectable neo marker inserted into the retroviral vector MFG.
Figure 3:
FIG. 3 shows a micrograph of synovium recovered from the knee of a rabbit approximately one month after intra-articular injection of Lac $Z^+$, neo synoviocytes employing the methods of this invention.

FIG. 2 shows the cDNA encoding the human interleukin-1 receptor antagonist protein (IRAP) with a selectable neo gene marker. FIG. 3 shows a low power micrograph of synovium recovered from the knee of a rabbit one month after intra-articular injection of Lac $Z^+$, $neo^+$ synoviocytes. Tissue was stained histochemically for the presence of beta-galactosidase. This micrograph counterstained with resin revealed an area of intensely stained, transplanted cells demonstrating that these cells have colonized the synovial lining of the recipient joint.

EXAMPLE IV
Animal Models

The methods of this invention of transferring genes to the synovia of mammalian joints permit the production and analysis of joint pathologies that were not previously possible. This is because the only other way of delivering potentially arthriotogenic compounds to the joint is by intra-articular injection. Not only are such compounds quickly cleared from joints, but the effects of bolus injections of these compounds do not accurately mimic physiological conditions where they are constantly produced over a long period of time. In contrast, the gene transfer technologies of this invention permit selected proteins of known or suspected involvement in the arthritic process to be expressed intra-articularly over an extended period of time, such as for example, at least a three month period. The animal models of this invention therefore permits the importance of each gene product to the arthritic process to be evaluated individually. Candidate genes include, but are not restricted to, those coding for cytokines such as interleukin-1 (IL-1) alpha, IL-1 beta, and TNF-alpha, and matrix metalloproteinases such as collagenases, gelatinases and stromelysins.

Additionally, the gene transfer techniques of this invention are suitable for use in the screening of potentially therapeutic proteins. In this use, the animal models of the invention are initiated in joints whose synovia express gene coding for potential anti-arthritic proteins. Candidate proteins include, but are not restricted to, inhibitors of proteinases such as, for example, the tissue inhibitor of metalloproteinases, and cytokines such as, for example, transforming growth factor-beta.

EXAMPLE V
Method For Using Synoviocytes As A Delivery System For Gene Therapy Rabbits are killed by intravenous injection of 4 ml nembutol, and their knees quickly shaved. Synovia are surgically removed from each knee under aseptic conditions, and the cells removed from their surrounding matrix by sequential digestion with trypsin and collagenase (0.2% w/v in Gey's Balanced Salt Solution) for about 30 minutes and about 2 hours, respectively. The cells recovered in this way are seeded into 25 $cm^2$ culture flasks with about 4 ml of Ham's $F_{12}$ nutrient medium supplemented with 10% fetal bovine serum, about 100 U/ml penicillin and about 100 ) μg/ml streptomycin, and incubated at about 37° in an atmosphere of 95% air, 5% $CO_2$. Following about 3–4 days incubation, the cells attain confluence. At this stage, the culture medium is removed and the cell sheet washed twice with approximately 5 mls of Gey's Balanced Salt Solution to remove non-adherent cells such as lymphocytes. The adherent cells are then treated with trypsin (0.25% w/v in balanced salt solution). This treatment detaches the fibroblastic, Type B synoviocytes, but leaves macrophages, polymorphonuclear leukocytes and the Type A synoviocytes attached to the culture vessel. The detached cells are recovered, re-seeded into 25 $cm^2$ culture vessels at a 1:2 split ratio, medium is added and the culture returned to the incubator. At confluence this procedure is repeated.

After the third such passage, the cells are uniformly fibroblastic and comprise a homogeneous population of Type B synoviocytes. At this stage, cells are infected with the retroviral vector.

Following infection, cells are transferred to fresh nutrient medium supplemented with about 1 mg/ml G418 (GIBCO/BRL, P.O. Box 68, Grand Island, N.Y. 14072-0068) and returned to the incubator. Medium is changed every three days as $neo^-$ cells die and the $neo^+$ cells proliferate and attain confluency. When confluent, the cells are trypsinized and subcultured as described above. One flask is set aside for staining with X-gal to confirm that the $neo^+$ cells are also Lac $Z^+$. When the subcultures are confluent, the medium is recovered and tested for the presence of IRAP, soluble IL-1R or other appropriate gene products as hereinbefore described. Producing synoviocyte cultures are then ready for transplantation.

The day before transplantation, the cells are recovered by trypsinizing, as hereinbefore described. These cells are then suspended in nutrient medium, and incubated overnight in an untreated plastic centrifuge tube. Under these conditions, the cells do not adhere, but they regenerate their cell surface proteins that were removed by trypsinizing.

The following morning, the cells are recovered by centrifuging, washed several times by resuspension in Gey's Balanced Salt Solution and finally resuspended at a concentration of about $10^6$–$10^7$ cells/ml in Gey's solution. Approximately 1 ml of this suspension is then introduced into the knee joint of a recipient rabbit by intra-articular injection. For this purpose a 1 ml syringe with a 25-gauge hypodermic needle is used. Injection is carried out through the patellar tendon. Experiments in which radioopaque dye was injected have confirmed that this method successfully introduces material into all parts of the joint.

EXAMPLE VI

The method of Example V for producing generally uniformly fibroblastic cells of a homogeneous population of Type B synoviocytes was followed to effect growing cultures of lapine synovial fibroblasts. These growing cultures of lapine synovial fibroblasts were subsequently infected with an amphotropic retroviral vector carrying marker genes coding for beta-galactosidase (Lac Z) and resistance to the neomycin analogue G418 ($neo^+$). Following infection and growth in selective medium containing about 1 mg/ml G418, all cells stained positively in a histochemical stain for beta-galactosidase.

Neo selected cells carrying the Lac Z marker gene were transplanted back into the knees of recipient rabbits to examine the persistence and expression of these genes in vivo. Two weeks following transplantation, islands of Lac Z⁺ cells within the synovium of recipient knees were observed. This confirmed the ability of the method of this invention to introduce marker genes into rabbit synovia and to express them in situ.

EXAMPLE VII

Neo-selected, Lac Z⁺ synoviocytes were recovered from cell culture, suspended in Gey's Balanced Salt Solution and injected intra-articularly into the knee joints of recipient rabbits (about $10^5$–$10^7$ cells per knee). Contra-lateral control knees received only a carrier solution. At intervals up to 3 months following transplant, the rabbits were killed and their synovia and surrounding capsule recovered. Each sample may be analyzed in three ways. A third of the synovium was stained histochemically en masse for the presence of beta-galactosidase. A second portion may be used for immunocytochemistry using antibodies specific for bacterial beta-galactosidase. The final portion may be digested with trypsin and collagenase, and the cells thus recovered cultured in the presence of G418.

Staining of the bulk synovial tissue revealed extensive areas of Lac Z⁺ cells, visible to the naked eye. Control synovia remained colorless. Histochemical examination of synovia revealed the presence of islands of cells staining intensely positive for beta-galactosidase. These cells were present on the superficial layer of the synovial lining, and were absent from control synovia. From such tissue it was possible to grow Lac Z⁺, neo⁺ cells. Cells recovered from control tissue were Lac Z⁻ and died when G418 was added to the culture. This indicates that the transplanted, transduced synovial fibroblasts have successfully recolonized the synovia of recipient joints, and continue to express the two marker genes, Lac Z and neo. Maintaining intra-articular Lac Z and neo expression in transplanted synoviocytes has been effected for 3 months using primary cells and one month using the HIG-82 cell line.

EXAMPLE VIII

Based upon the methods of the hereinbefore presented examples, and employing standard recombinant techniques well known by those skilled in the art, the human IRAP gene was incorporated into an MFG vector as shown in FIG. 1. Following the infection of synoviocyte cultures of rabbit origin with this viral vector, IRAP was secreted into the culture medium.

Figure 4:
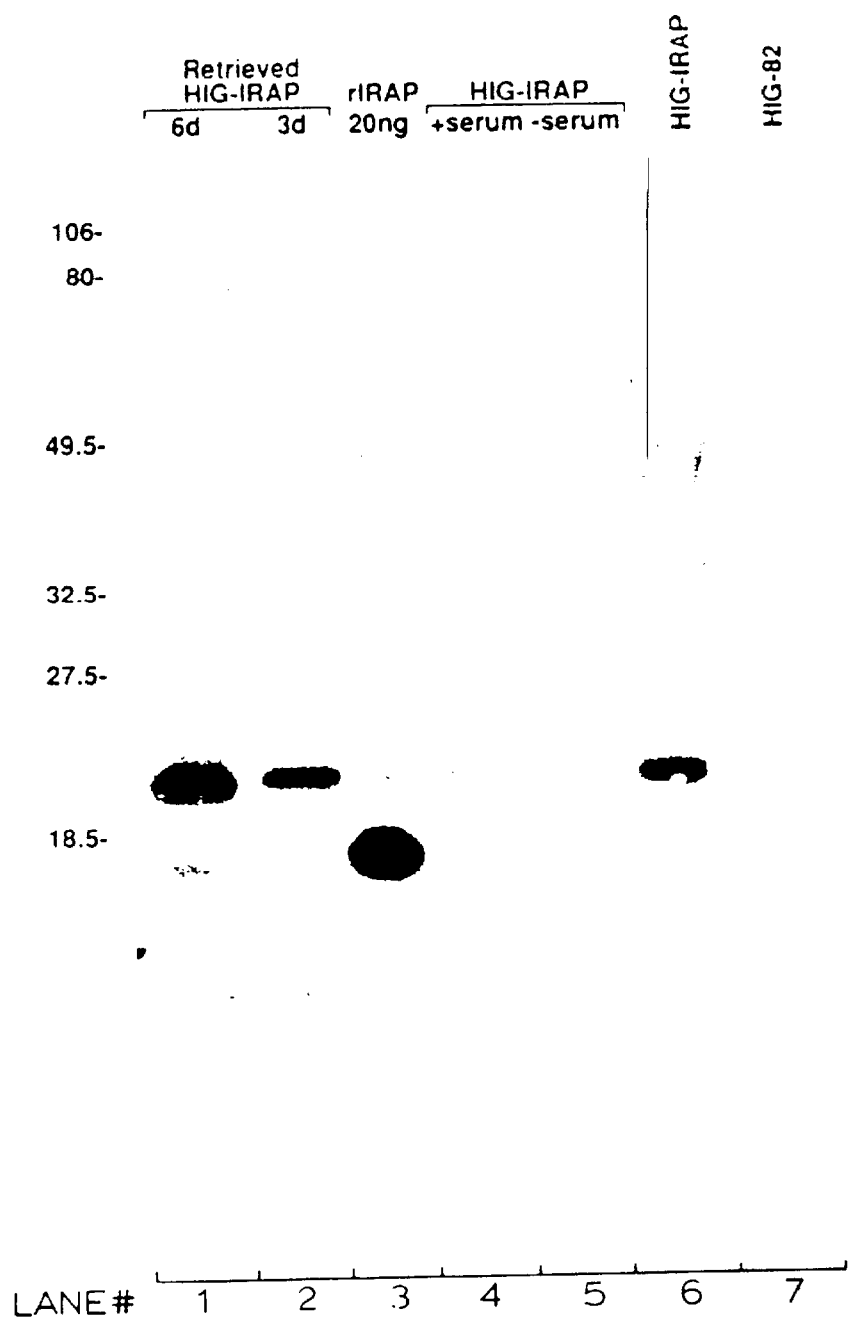
FIG. 4 shows a Western blot demonstrating the production of interleukin-1 receptor antagonist protein by four cultures of HIG-82 cells (Georgescu 1988) infected using the method of this invention employing the MFG-IRAP viral vector.

Western blotting, well known by those skilled in the art, was carried out using an IRAP-specific rabbit polyclonal antibody that does not recognize human or rabbit IL-1 alpha or IL-1 beta, or rabbit IRAP. FIG. 4 shows a Western blot which sets forth the production of IRAP by four cultures of HIG-82 cells infected with MFG-IRAP. Three forms of the IRAP are present: a non-glycosylated form which runs with recombinant standards, and two larger glycosylated forms. The results of the Western blotting shown in FIG. 4 demonstrated that IRAP was produced by HIG-82 synoviocyte cell line (Georgescu, 1988) following infection with the MFG-IRAP vector of this invention. The Western blotting of FIG. 4 shows the IRAP concentration of the conditioned medium is as high as 50 ng/ml. This is approximately equal to 500 ng IRAP/$10^6$ cells/day. Lane 1 and Lane 2 of FIG. 4 show that the recipient synovia tissue secrete substantial amounts of HIG-IRAP at 3 days (Lane 2) and 6 days (Lane 1). Lane 3 shows human recombinant IRAP. Lane 6 indicates that rabbit synovial cells produce a larger glycosylated version of this molecule after infection with MFG-IRAP. Lane 7 indicates that native rabbit synovial cells do not produce this glycosylated form.

FIG. 5 shows that medium conditioned by IRAP⁺ synoviocytes blocks the induction of neutral metalloproteinases in articular chondrocytes exposed to recombinant human IL-1 beta. Chondrocytes normally secrete 1 U/$10^6$ cells, or less, gelatinase into their culture media. FIG. 5 shows that when to about 5 U/ml or 10 U/ml IL-1 are added, gelatinase production increases to over 4 U and 6 U/$10^8$ cells, respectively. Addition of medium conditioned by MFG-IRAP-infected HIG-82 cells employed by the method of this invention suppressed gelatinase production by IL-1 treated chondrocytes. With 5 U/ml IL-1 (FIG. 5, right panel) inhibition was 100% for one culture and 41% for the other. With 10 U/ml IL-1, inhibition was reduced to 38% and 18% (FIG. 5, left panel) as is expected of a competitive inhibitor. These data demonstrate that the IRAP produced by HIG-82 cells infected with MFG-IRAP is biologically active.

EXAMPLE IX

This example demonstrates the uptake and expression of Lac Z gene by synoviocytes using infection by a liposome (lipofection). A six well plate containing synoviocyte cultures were transduced with the Lac Z gene by lipofection. The content of each well is as follows:

| Well 1 | Control cells, treated with liposomes alone |
|---|---|
| Well 2 | Control cells, treated with DNA alone |
| Well 3 | DNA + 150 nmole liposomes |
| Well 4 | DNA + 240 nmole liposomes |
| Well 5 | DNA + 300 nmole liposomes |
| Well 6 | DNA + 600 nmole liposomes |

Figure 6:
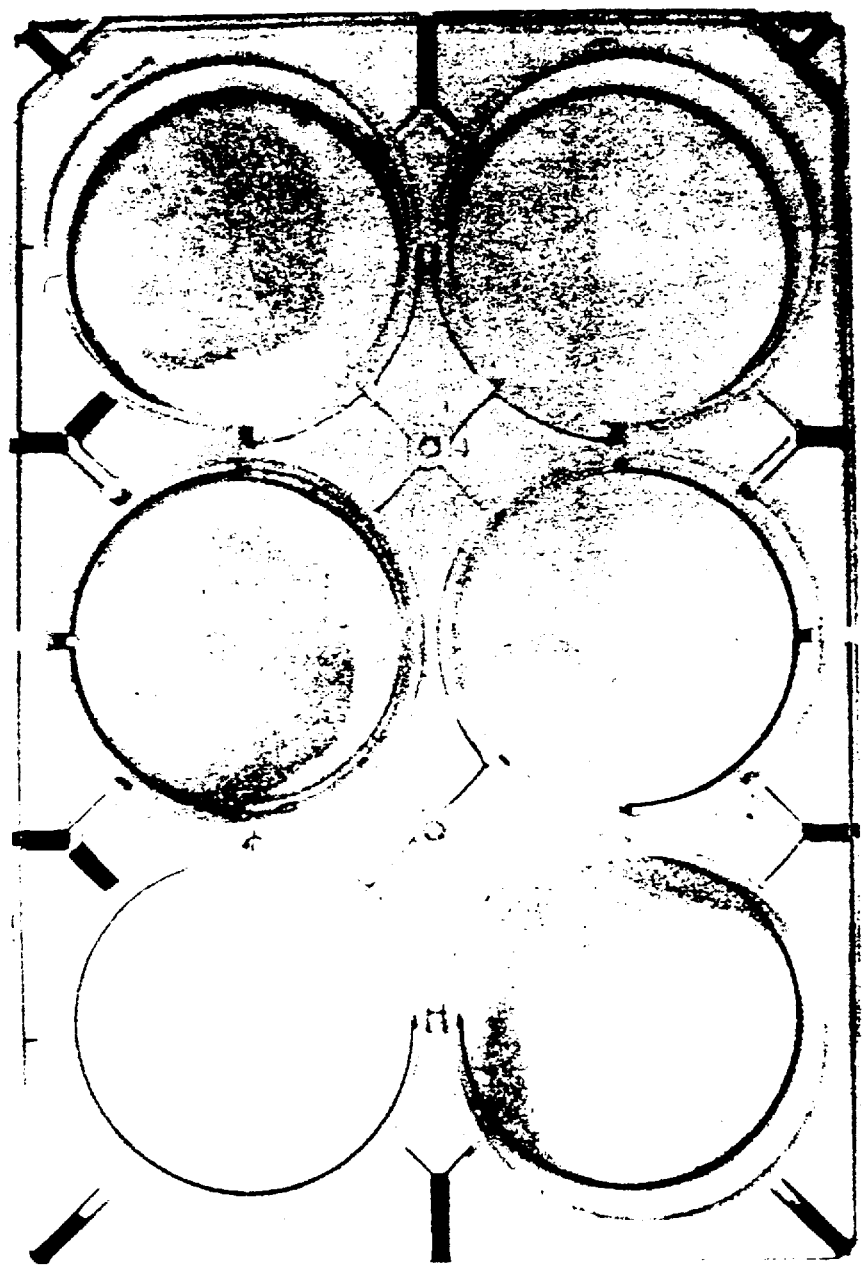
FIG. 6 shows the uptake and expression of the Lac Z gene by synoviocytes using lipofection. Well 1—Control cells, treated with liposomes alone; Well 2—Control cells, treated with DNA alone; Well 3—DNA+150 nmole liposomes; Well 4—DNA+240 nmole liposomes; Well 5—DNA+300 nmole liposomes; Well 6—DNA+600 nmole liposomes.

Wells 3–6 containing sub-confluent cultures of synovial fibroblasts were infected with 6 ug of DNA complexed with 150–600 nmoles/well of "DC-chol" liposome or in the alternative, with "SF-chol". Three days later, cells were stained histochemically for expression of beta-galactosidase (FIG. 6).

Table 1 shows the results of using the liposomes "DC-chol" and "SF-chol" in converting synoviocyte cultures to the Lac Z⁺ phenotype without selection. Table 1 sets forth that the "DC-chol" liposome in a concentration of about 300 nmole/well converted generally 30% of the synovial cells in synoviocyte cultures to the Lac Z⁺ phenotype without selection. Reduced expression was shown in Well 6 for "DC-chol" due to the toxic effect of the high liposome concentration.

TABLE 1

| Liposome, | % Lac Z⁺ Cells | |
|---|---|---|
| nmole/well | DC-chol | SF-chol |
| 150 | 10 | 0.5 |
| 240 | 22 | 1.0 |
| 300 | 30 | 2.8 |
| 600 | NA | 3.5 |

In another embodiment of this invention, a gene and method of using this gene provides for the neutralization of interleukin-1. Interleukin-1 is a key mediator of cartilage destruction in arthritis. Interleukin-1 also causes inflammation and is a very powerful inducer of bone resorption. Many of these effects result from the ability of interleukin-1 to increase enormously the cellular synthesis of prostaglandin E$_2$, the neutral proteinases—collagenase, gelatinase, and stromelysin, and plasminogen activator. The catabolic effects of interleukin-1 upon cartilage are exacerbated by its ability to suppress the synthesis of the cartilaginous matrix by chondrocytes. Interleukin-1 is present at high concentrations in synovial fluids aspirated from arthritic joints and it has been demonstrated that intra-articular injection of recombinant interleukin-1 in animals causes cartilage breakdown and inflammation.

Figure 7:
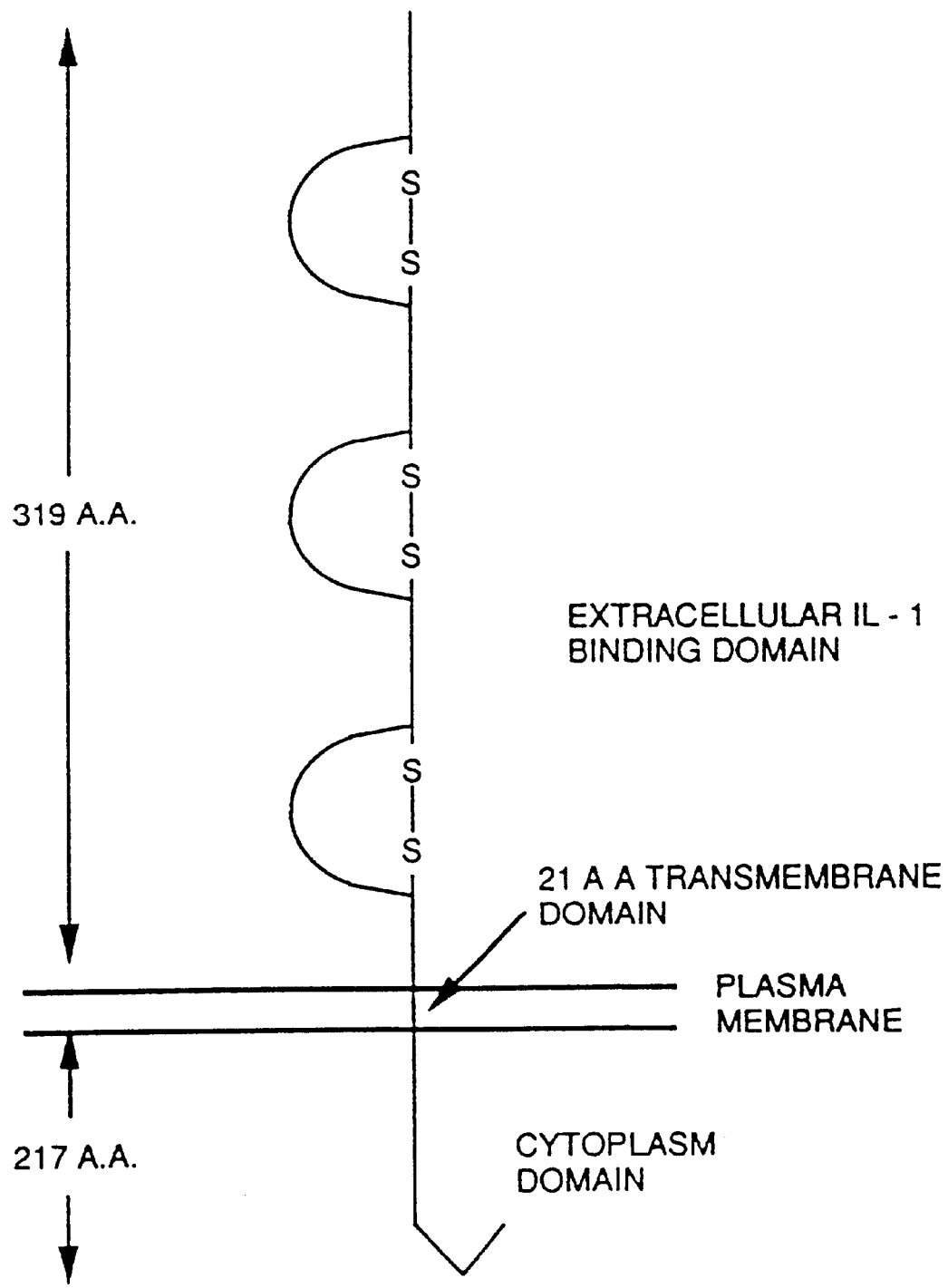
FIG. 7 shows the interleukin-1 binding domain amino acid arrangement.
Figure 8A:
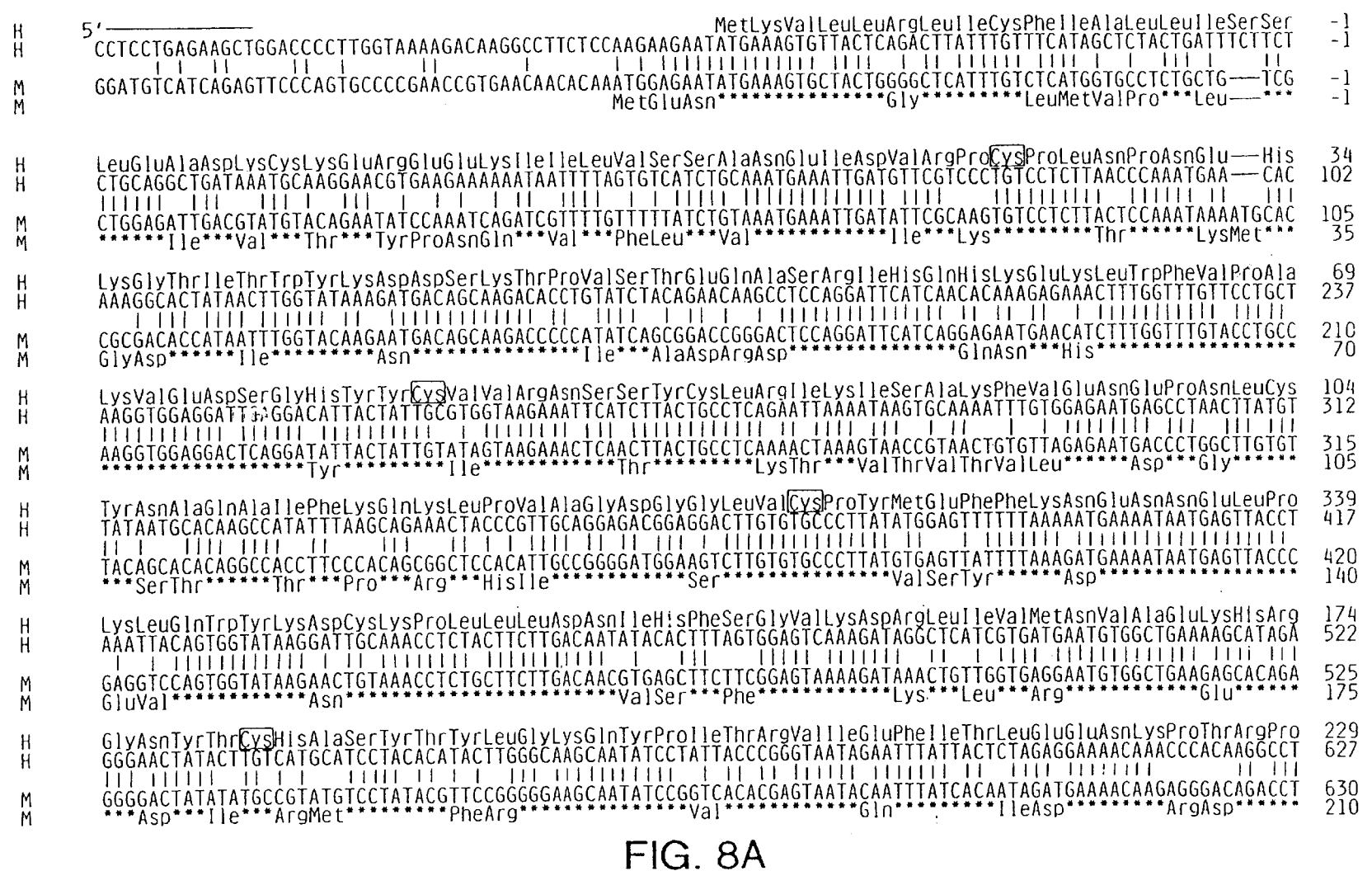
Figure 8B:
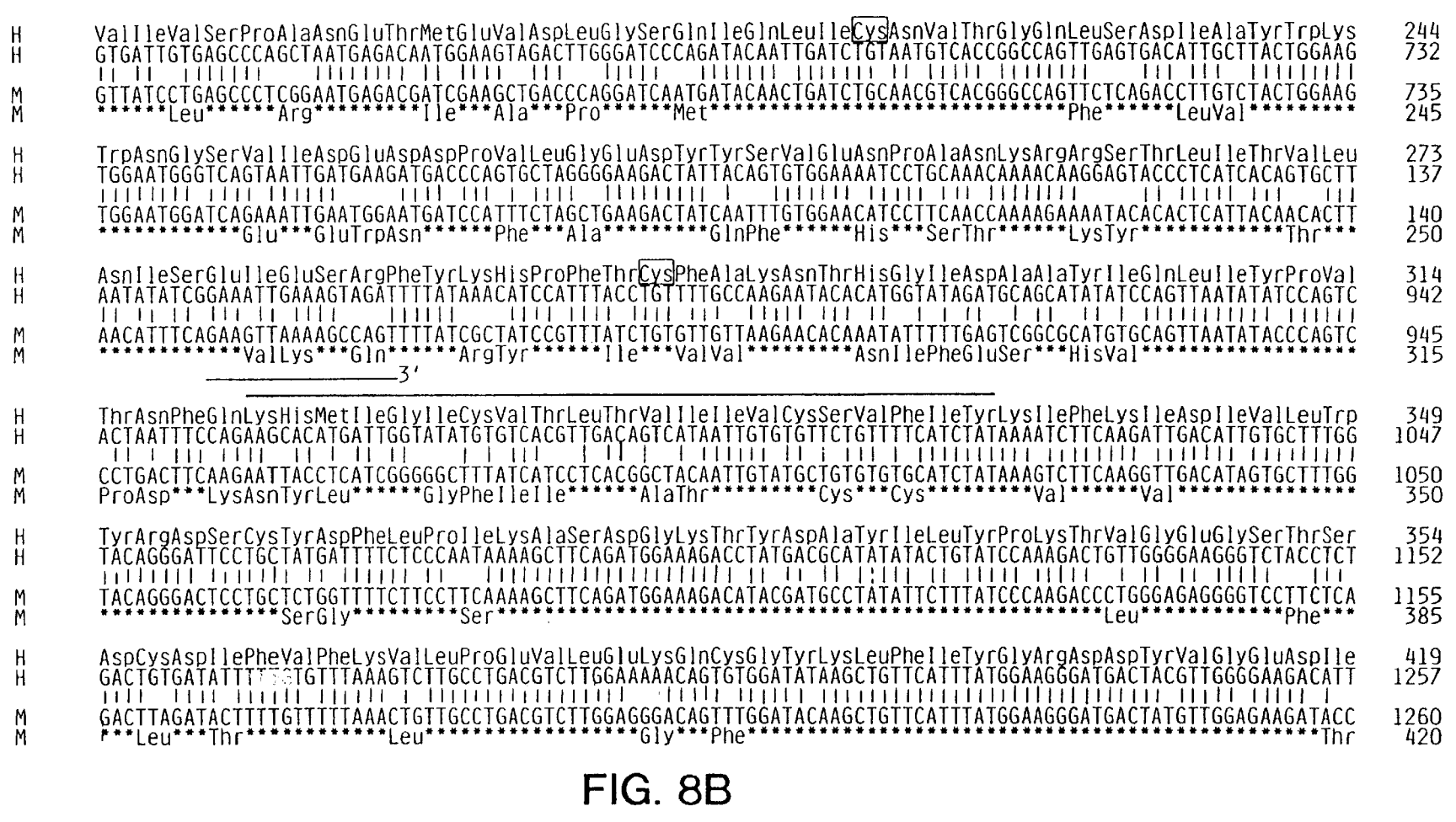
Figure 8C:
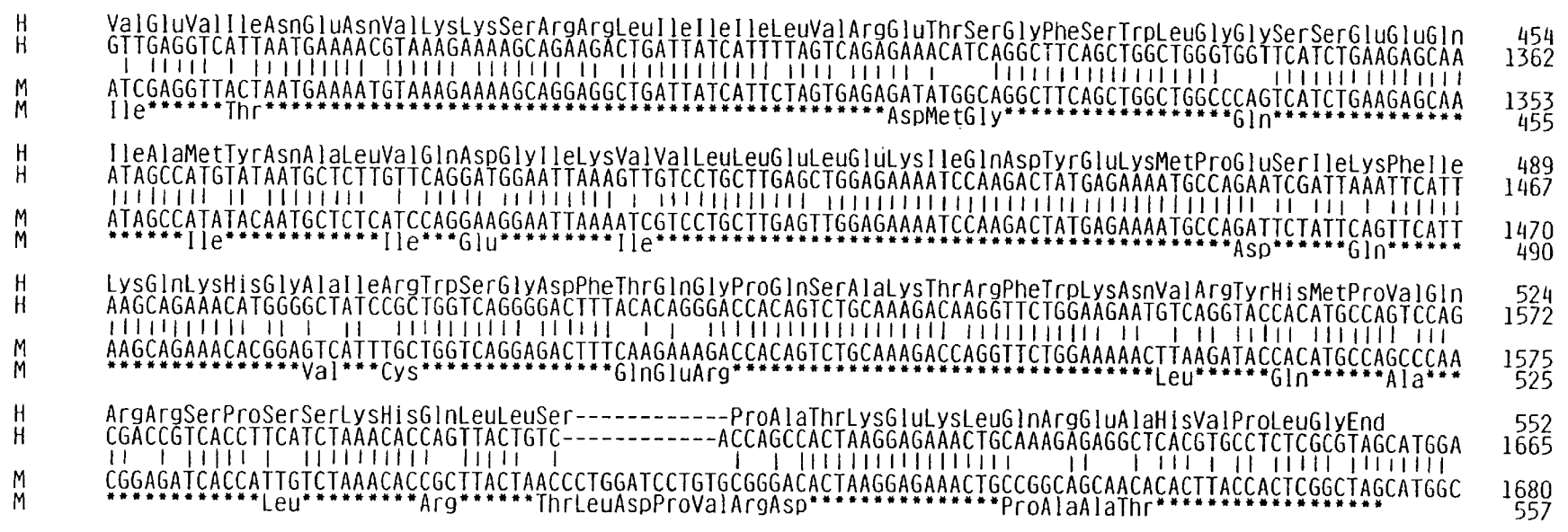

Interleukin-1 exists as several species, such as unglycosylated polypeptide of 17,000 Daltons. Two species have previously been cloned, interleukin-1 alpha and interleukin-1 beta. The alpha form has a pI of approximately 5, and the beta form has a pI around 7. Despite the existence of these isoforms, interleukin-1 alpha and interleukin-1 beta have substantially identical biological properties and share common cell surface receptors. The type I interleukin-1 receptor is a 80 kDa (kilodalton) glycoprotein and contains an extracellular, interleukin-1 binding portion of 319 amino acids which are arranged in three immunoglobulin-like domains held together by disulfide bridges as shown in FIG. 7. A 21 amino acid trans-membrane domain joins the extracellular portion to the 217 amino acid cytoplasmic domain. FIGS. 8A–8C show the amino acid and nucleotide sequence of the human and mouse interleukin-1 receptors. In FIG. 8B, the 21 amino acid trans-membrane region of the interleukin-1 receptor is marked by the thicker solid line. In FIGS. 8A and 8B, the position of the 5' and 3' oligonucleotides for PCR are marked by thinner short lines, respectively. The lysine amino acid just 5' to the trans-membrane domain to be mutated to a stop codon is marked by a solid circle in FIG. 8B.

Synovium is by far the major, and perhaps the only, intra-articular source of interleukin-1 in the arthritic joint. Snyovia recovered from arthritic joints secrete high levels of interleukin-1. Both the resident synoviocytes and infiltrating blood mononuclear cells within the synovial lining produce interleukin-1.

The present invention provides a method of using in vivo a gene coding for a truncated form of the interleukin-1 receptor which retains its ability to bind interleukin-1 with high affinity but which is released extracellularly and therefore inactive in signal transduction. The binding of this truncated and modified receptor to interleukin-1 inhibits the intra-articular activity of interleukin-1.

This method of using a gene encoding the extracellular interleukin-1 binding domain of an interleukin-1 receptor that is capable of binding to and neutralizing interleukin-1 includes employing a retroviral vector carrying a truncated interleukin-1 receptor gene which encodes a truncated and soluble active form of the receptor. The expression of the novel interleukin-1 receptor gene is controlled by regulatory sequences contained within the vector that are active in eukaryotic cells. This recombinant viral vector is transfected into cell lines stably expressing the viral proteins in trans required for production of infectious virus particles carrying the recombinant vector. These viral particles are used to deliver the recombinant interleukin-1 receptor to the recipient synovial cells by direct virus infection in vivo.

The soluble human interleukin-1 receptor to be inserted into the retroviral vector may be generated by a polymerase chain reaction (PCR). An oligonucleotide complementary to the 5' leader sequence of the human interleukin-1 receptor (GCGGATCCCCTCCTGAGAAGCT; SEQ ID NO:5) and an oligonucleotide complementary to a region just upstream from the transmembrane domain of the interleukin-1 receptor (GCGGATCCCATGTGCTACTGG; SEQ ID NO: 6) are used as primers for PCR. The primer for the region of the interleukin-1 receptor adjacent to the trans-membrane domain contains a single base change so that the lys codon at amino acid 336 of SEQ ID NOS: 1 and 2 (AAG) is changed to a stop codon (TAG). By inserting a translation stop codon just upstream from the transmembrane domain, a truncated form of interleukin-1 receptor that is secreted by the cell is generated. A BamHI recognition sequence (GGATCC) is added to the 5' end of the PCR primers, and following amplification, the resulting interleukin-1 receptor fragment is cloned into a BamHI site. A cDNA library from human T-cells is used as a source for the interleukin-1 receptor cDNA. To amplify the appropriate region of the interleukin-1 receptor from the cDNA library, the complementary primers are added to the DNA and 50 cycles of annealing, primer extension and denaturation are performed using a thermocycler and standard PCR reaction. conditions well known by those persons skilled in the art. Following amplification of the interleukin-1 soluble receptor using the PCR process, the resulting fragment is digested with BamHI and inserted into the pLJ retroviral vector. The pLJ retroviral vector is available from A. J. Korman and R. C. Mulligan. See also *Proc. Natl. Acad. Sci.,* Vol. 84, pp. 2150–2154 (April 1987) co-authored by Alan J. Korman, J. Daniel Frantz, Jack L. Strominger and Richard C. Mulligan. Restriction analysis was performed to determine the correct orientation of the insert.

The retrovirus vector carrying the truncated interleukin-1 receptor is transferred into the CRIP (*Proc. Natl. Acad. Sci.,* Vol. 85, pp. 6460–6464 (1988), O. Danos and R. C. Mulligan) packaging cell line using a standard CaPO$_4$ transfection procedure and cells wherein the viral vector is stably integrated and is selected on the basis of resistance to the antibiotic G418. The viral vector containing the neomycin resistant (neo-r) gene is capable of imparting resistance of the cell line to G418. The CRIP cell line expresses the three viral proteins required for packaging the vector viral RNAs into infectious particles. Moreover, the viral particles produced by the CRIP cell line are able to efficiently infect a wide variety of mammalian cell types including human cells. All retroviral particles produced by this cell line are defective for replication but retain the ability to stably integrate into synovial cells thereby becoming an heritable trait of these cells. Virus stocks produced by this method are substantially free of contaminating helper-virus particles and are also non-pathogenic.

Figure 9:
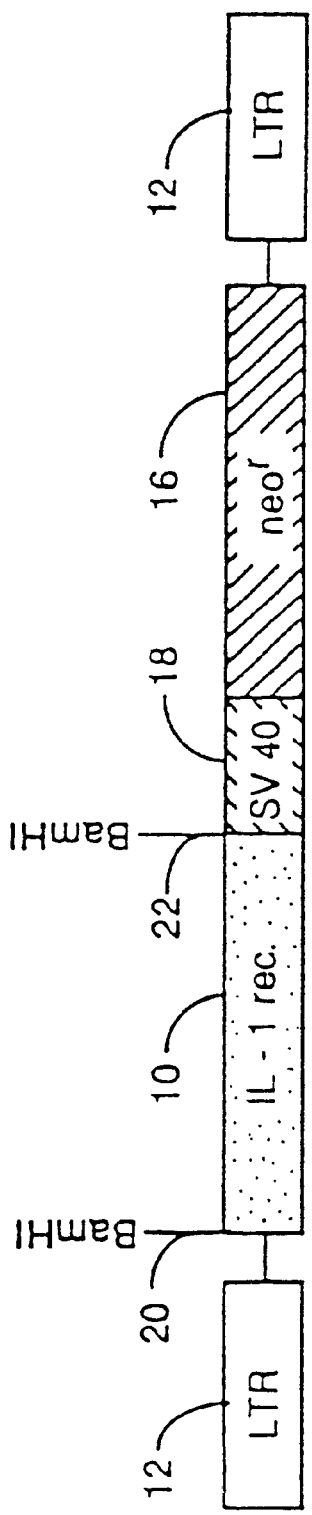
FIG. 9 shows gene encoding a truncated interleukin-1 receptor inserted into a retroviral vector.

More specifically, the truncated interleukin-1 gene can be inserted into a retroviral vector under the regulation of a suitable eukaryotic promoter such as the retroviral promoter already contained within the gene transfer vector, such as for example, the pLJ vector shown in FIG. 9. FIG. 9 shows the structure of the pLJ interleukin receptor retroviral vector and partial restriction endonuclease map. Reference numeral 10 shows the interleukin-1 receptor inserted into a retroviral vector. Reference numeral 12 indicates long terminal repeats (LTR's) at each end of the structure of the pLJ interleukin receptor retroviral vector shown in FIG. 8. These LTR's regulate the viral transcription and expression of the interleukin-1 receptor. Bacterial gene encoding resistance to the antibiotic neomycin (neo-r) is shown at reference numeral 16. The Simian Virus 40 enhancer promoter (SV 40) is indicated at reference numeral 18, and regulates the expression of the neo-r gene. Reference numbers 20 and 22, respectively, show the sites wherein the resulting interleukin receptor fragment is cloned. It will be understood by those persons skilled in the art that other vectors containing different eukaryotic promoters may also be utilized to obtain a generally maximal level of interleukin-1 receptor expression. The vectors containing the truncated, and modified interleukin-1 receptor will be introduced into a retroviral packaging cell line (CRIP) by transfection and stable transformants isolated by selection for the expression of the neomycin resistance gene also carried by the pLJ vector. The CRIP cell line expresses all the proteins required for packaging of the exogenous retroviral RNA. Viral particles produced by the G418-selected CRIP cell lines will carry a recombinant retrovirus able to infect mammalian cells and stably express the interleukin-1 truncated receptor. The viral particles are used to infect synovial cells directly in vivo by injecting the virus into the joint space.

Another embodiment of this invention provides a method for using the hereinbefore described viral particles to infect in culture synovial cells obtained from the lining of the joint of a mammalian host. The advantage of the infection of synovial cells in culture is that infected cells harboring the interleukin-1 receptor retroviral construct can be selected using G418 for expression of the neomycin resistance gene. The infected synovial cells expressing the interleukin-1 receptor can then be transplanted back into the joint by intra-articular injection. The transplanted cells will express high levels of soluble interleukin-1 receptor in the joint space thereby binding to and neutralizing substantially all isoforms of interleukin-1, including interleukin-1 alpha and interleukin-1 beta.

The method used for transplantation of the synovial cells within the joint is a routine and relatively minor procedure used in the treatment of chronic inflammatory joint disease. Although synovium can be recovered from the joint during open surgery, it is now common to perform synovectomies, especially of the knee, through the arthroscope. The arthroscope is a small, hollow rod inserted into the knee via a small puncture wound. In addition to permitting the intra-articular insertion of a fibre-option system, the arthroscope allows access to surgical instruments, such that snyovial tissue can be removed arthroscopically. Such procedures can be carried out under "spinal" anesthetic and the patient allowed home the same day. In this manner sufficient synovium can be obtained from patients who will receive this gene therapy.

The synovial cells (synoviocytes) contained within the excised tissue may be aseptically recovered by enzymic digestion of the connective tissue matrix. Generally, the synovium is cut into pieces of approximately 1 millimeter diameter and digested sequentially with trypsin (0.2% w/v in Gey's Balanced Salt Solution) for 30 minutes at 37° Centigrade, and collagenase (0.2% w/v in Gey's Balanced Salt Solution) for 2 hours at 37° Centigrade. Cells recovered from this digestion are seeded into plastic culture dishes at a concentration of $10^4$–$10^5$ cells per square centimeter with Hank's $F_{12}$ medium supplemented with 10% fetal bovine serum and antibiotics. After 3–7 days, the culture medium is withdrawn. Non-adherent cells such as lymphocytes are removed by washing with Gey's Balanced Salt Solution and fresh medium added. The adherent cells can now be used as they are, allowed to grow to confluency or taken through one or more subcultures. Subcultivating expands the cell number and removes non-dividing cells such as macrophages.

Following genetic manipulation of the cells thus recovered, they can be removed from the culture dish by trypsinizing, scraping or other means, and made into a standard suspension. Gey's Balanced Salt Solution or other isotonic salt solutions of suitable composition, or saline solution are suitable carriers. A suspension of cells can then be injected into the recipient mammalian joint. Intra-articular injections of this type are routine and easily carried out in the doctor's office. No surgery is necessary. Very large numbers of cells can be introduced in this way and repeat injections carried out as needed.

Another embodiment of this invention is the gene produced by the hereinbefore described method of preparation. This gene carried by the retrovirus may be incorporated in a suitable pharmaceutical carrier, such as for example, buffered physiologic saline, for parenteral administration. This gene may be administered to a patient in a therapeutically effective dose. More specifically, this gene may be incorporated in a suitable pharmaceutical carrier at a therapeutically effective dose and administered by intra-articular injection.

In another embodiment of this invention, this gene may be administered to patients as a prophylactic measure to prevent the development of arthritis in those patients determined to be highly susceptible of developing this disease. More specifically, this gene carried by the retrovirus may be incorporated in a suitable pharmaceutical carrier at a prophylactically effective dose and administered by parenteral injection, including intra-articular injection.

EXAMPLE X

Fifty micrograms of a DNA plasmid vector molecule containing the interleukin-1 beta coding sequence ligated downstream of the CMV promoter was encapsulated within cationic liposomes, mixed with Geys biological buffer and injected intra-articularly into the knee joints of a rabbit. Fourty eight hours subsequent to injection one nanogram of interleukin-1 beta was recovered from the knee joint area. Therefore, injection of the DNA containing liposome solution within the region of the synovial tissue prompted fusion of the liposomes to the synovial cells, transfer of the DNA plasmid vector into synovial cells and subsequent expression of the IL-1 beta gene. Additionally, it is possible to inject non-encapsulated (i.e., naked) DNA into the joint area and monitor transfection of the DNA vector into the synovial cells as determined by subsequent expression of the IL-1 beta gene in synovial cells. Therefore, either method may be utilized as a plausible alternative to the in vitro manipulation of synovia also exemplified in the present invention.

It will be appreciated by those skilled in the art that this invention provides a method of introducing into a connective tissue cell of a mammalian host in vitro, or in the alternative in vivo, at least one gene which codes for proteins with therapeutic properties. This method includes employing genes having DNA that is capable of maintenance and expression.

It will be appreciated by those skilled in the art that this invention provides a method of introducing at least one gene encoding a product into at least one cell of the connective tissue of a mammalian host for treating an arthritic condition of the mammalian host.

It will be understood by those skilled in the art that this invention provides a method to repair and regenerate the connective tissue of a mammalian host.

It will be further understood that this invention provides a method to produce an animal model for the study of connective tissue pathology.

It will be appreciated by those persons skilled in the art that this invention provides a method of using and a method of preparing a gene encoding an extra cellular interleukin-1 binding domain of an interleukin-1 receptor that is capable of binding to and neutralizing substantially all isoforms of interleukin-1, and thus substantially protect cartilage of a mammalian host from pathological degradation. In addition, it will be understood by those persons skilled in the art that the method of using the gene of this invention will reduce inflammation, protect soft tissues of the joint and suppress the loss of bone that occurs in patients suffering with arthritis.

It will be appreciated by those persons skilled in the art that the viral vectors employed in the hereinbefore described invention may be employed to transfect synovial cells in vivo or in culture, such as by direct intra-articular injection or transplantation of autologous synovial cells from the patient transduced with the retroviral vector carrying the truncated interleukin-1 receptor gene.

Whereas particular embodiments of this invention have been described above for purposes of illustration, it will be evident to those persons skilled in the art that numerous variations of the details of the present invention may be made without departing from the invention as defined in the appended claims.

We claim:

1. A method for inhibiting leukocyte infiltration or cartilage degradation in a joint of a mammal, the method comprising directly administering to said joint a viral vector comprising a nucleic acid sequence, operably linked to a promoter, encoding a protein that counteracts an effect of IL-1 in a joint, wherein expression of said protein within said joint results in an inhibition of leukocyte infiltration or cartilage degradation in said joint.

2. The method of claim 1, wherein said protein is an interleukin-1 receptor antagonist protein (IRAP) or a biologically active fragment or biologically active derivative thereof.

3. The method of claim 1, wherein said protein is a soluble interleukin-1 receptor or a biologically active fragment or biologically active derivative thereof.

4. The method of claim 1, wherein said protein is a soluble TNF receptor or a biologically active fragment or biologically active derivative thereof.

5. The method of claim 1, wherein said protein is interleukin-10 or a biologically active fragment or biologically active derivative thereof.

6. The method of claim 1, wherein said vector is introduced into said joint by intra-articular injection.

7. The method of claim 1, wherein said viral vector is a retroviral vector.

8. The method of claim 1, wherein said viral vector is an adenoviral vector.

9. The method of claim 1, wherein said viral vector is a herpes simplex viral vector.

* * * * *